United States Patent
Dong

(10) Patent No.: US 8,299,022 B2
(45) Date of Patent: Oct. 30, 2012

(54) ANALOGS OF GHRELIN SUBSTITUTED AT THE N-TERMINAL

(75) Inventor: Zheng Xin Dong, Holliston, MA (US)

(73) Assignee: IPSEN Pharma S.A.S., Boulogne (FR)

( * ) Notice: Subject to any disclaimer, the term of this patent is extended or adjusted under 35 U.S.C. 154(b) by 610 days.

(21) Appl. No.: 12/311,409

(22) PCT Filed: Sep. 24, 2007

(86) PCT No.: PCT/US2007/020595
§ 371 (c)(1), (2), (4) Date: Mar. 27, 2009

(87) PCT Pub. No.: WO2008/039415
PCT Pub. Date: Apr. 3, 2008

(65) Prior Publication Data
US 2009/0275511 A1    Nov. 5, 2009

Related U.S. Application Data

(60) Provisional application No. 60/847,423, filed on Sep. 27, 2006.

(51) Int. Cl.
| | |
|---|---|
| *A61K 38/22* | (2006.01) |
| *A61K 38/27* | (2006.01) |
| *A61K 38/16* | (2006.01) |
| *C07K 14/00* | (2006.01) |
| *C07K 14/61* | (2006.01) |

(52) U.S. Cl. ............ 514/4.8; 514/1.1; 514/4.9; 514/5.3; 514/21.3; 530/324

(58) Field of Classification Search .................. None
See application file for complete search history.

(56) References Cited

U.S. PATENT DOCUMENTS

| 8,076,281 B2 * | 12/2011 | Tulipano et al. .............. 514/1.7 |
| 2003/0186844 A1 | 10/2003 | Bednarek |
| 2005/0148515 A1 | 7/2005 | Dong |
| 2005/0272648 A1 | 12/2005 | Dong et al. |
| 2009/0163416 A1 * | 6/2009 | Tulipano et al. ................ 514/12 |

FOREIGN PATENT DOCUMENTS

| EP | 1197496 | 4/2002 |
| WO | 01/92292 | 12/2001 |
| WO | 2004/009616 | 1/2004 |
| WO | 2007/038678 | 4/2007 |

* cited by examiner

*Primary Examiner* — Julie Ha
(74) *Attorney, Agent, or Firm* — Yankwich & Associates; Tony K. Uhm; Pamela C. Ball

(57) ABSTRACT

The invention comprises peptidyl analogs of ghrelin having greater stability which are active at the GHS receptor according to formulae depicted below:

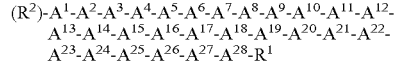

wherein the definitions of $A^1$ to $A^{28}$, $R^1$ and $R^2$ are provided for in the specification, with the exception that the N-terminal amino acid must be selected from the group consisting of Inp, 1-Apc and 4-Apc, the pharmaceutically acceptable salts thereof and pharmaceutical compositions comprising an effective amount of said compound together with therapeutic and non-therapeutic uses thereof.

27 Claims, No Drawings

```
                          SEQUENCE LISTING

<160> NUMBER OF SEQ ID NOS: 27

<210> SEQ ID NO 1
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 7
<212> TYPE: PRT
<213> ORGANISM: Artificial sequence
<220> FEATURE:
<223> OTHER INFORMATION: Growth hormone secretagogue
<220> FEATURE:
<221> NAME/KEY: MISC_FEATURE
<222> LOCATION: (3)..(3)
<223> OTHER INFORMATION: Xaa = D--(2'-naphthyl)-L-alanine (D-(2')-Nal)
<220> FEATURE:
<221> NAME/KEY: MISC_FEATURE
<222> LOCATION: (6)..(6)
<223> OTHER INFORMATION: Xaa = D-Phe
<220> FEATURE:
<221> NAME/KEY: MOD_RES
<222> LOCATION: (7)..(7)
<223> OTHER INFORMATION: AMIDATION

<400> SEQUENCE: 2

Ala His Xaa Ala Trp Xaa Lys
1               5

<210> SEQ ID NO 3
<211> LENGTH: 6
<212> TYPE: PRT
<213> ORGANISM: Artificial sequence
<220> FEATURE:
<223> OTHER INFORMATION: Growth hormone secretagogue
<220> FEATURE:
<221> NAME/KEY: MISC_FEATURE
<222> LOCATION: (1)..(1)
<223> OTHER INFORMATION: Xaa = D-Ala
<220> FEATURE:
<221> NAME/KEY: MISC_FEATURE
<222> LOCATION: (2)..(2)
<223> OTHER INFORMATION: Xaa = D--(2'-naphthyl)-L-alanine (D-(2')-Nal)
<220> FEATURE:
<221> NAME/KEY: MISC_FEATURE
```

```
<222> LOCATION: (5)..(5)
<223> OTHER INFORMATION: Xaa = D-naphthyl-alanine (D-Nal)
<220> FEATURE:
<221> NAME/KEY: MOD_RES
<222> LOCATION: (6)..(6)
<223> OTHER INFORMATION: AMIDATION

<400> SEQUENCE: 3

Xaa Xaa Ala Trp Xaa Lys
1               5

<210> SEQ ID NO 4
<211> LENGTH: 6
<212> TYPE: PRT
<213> ORGANISM: Artificial sequence
<220> FEATURE:
<223> OTHER INFORMATION: Growth hormone secretagogue
<220> FEATURE:
<221> NAME/KEY: MISC_FEATURE
<222> LOCATION: (2)..(2)
<223> OTHER INFORMATION: Xaa = D-2-methyl-tryptophan (D-Me-Trp)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 4

His Xaa Ala Trp Xaa Lys
1               5

<210> SEQ ID NO 5
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 5

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
```

```
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 6

Xaa Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 7
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MOD_RES
<222> LOCATION: (28)..(28)
<223> OTHER INFORMATION: AMIDATION

<400> SEQUENCE: 7

Xaa Xaa Glu Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 8
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 8

Xaa Xaa Ser Phe Leu Ser Pro Glu His Xaa Arg Val Gln Gln Arg Lys
```

```
                1               5                  10                 15
Glu Ser Lys Lys Pro Pro Ala Lys Leu Gln Pro Arg
            20                  25
```

<210> SEQ ID NO 9
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 9

```
Xaa Xaa Ser Phe Leu Ser Pro Xaa His Gln Arg Val Gln Gln Arg Lys
1               5                   10                  15
Glu Ser Lys Lys Pro Pro Ala Lys Leu Gln Pro Arg
            20                  25
```

<210> SEQ ID NO 10
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 10

```
Xaa Xaa Ser Phe Leu Ser Pro Glu His Gln Arg Val Gln Gln Arg Lys
1               5                   10                  15
Ser Ser Lys Lys Pro Pro Ala Lys Leu Gln Pro Arg
            20                  25
```

<210> SEQ ID NO 11
<211> LENGTH: 28

```
-continued

<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 11

Xaa Ser Ser Phe Leu Ser Pro Glu His Gln Arg Val Gln Gln Arg Lys
1               5                   10                  15
Ser Ser Lys Lys Pro Pro Ala Lys Leu Gln Pro Arg
            20                  25

<210> SEQ ID NO 12
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MISC_FEATURE
<222> LOCATION: (8)..(8)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 12

Xaa Xaa Ser Phe Leu Ser Pro Xaa His Gln Arg Val Gln Gln Arg Lys
1               5                   10                  15
Ser Ser Lys Lys Pro Pro Ala Lys Leu Gln Pro Arg
            20                  25

<210> SEQ ID NO 13
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
```

```
<220> FEATURE:
<221> NAME/KEY: MOD_RES
<222> LOCATION: (28)..(28)
<223> OTHER INFORMATION: AMIDATION

<400> SEQUENCE: 13

Xaa Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 14
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 14

Xaa Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 15
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (17)..(17)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 15

Xaa Xaa Ser Phe Leu Ser Pro Glu His Gln Arg Val Gln Gln Arg Lys
1               5                   10                  15

Ser Ser Lys Lys Pro Pro Ala Lys Leu Gln Pro Arg
            20                  25

<210> SEQ ID NO 16
<211> LENGTH: 28
<212> TYPE: PRT
<213> ORGANISM: Artificial
<220> FEATURE:
<223> OTHER INFORMATION: Peptidyl analog of ghrelin
```

```
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 16

Xaa Xaa Ser Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 17
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = isonipecotic acid (Inp)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 17

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 18
<211> LENGTH: 28
<212> TYPE: PRT
<213> ORGANISM: Artificial
<220> FEATURE:
<223> OTHER INFORMATION: Peptidyl ghrelin analog
<220> FEATURE:
<221> NAME/KEY: MISC_FEATURE
<222> LOCATION: (1)..(1)
<223> OTHER INFORMATION: Xaa = 1-Apc
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
```

```
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 18

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 19
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = isonipecotic acid (Inp) modified with
      acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
<223> OTHER INFORMATION: AMIDATION

<400> SEQUENCE: 19

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 20
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (1)..(1)
<223> OTHER INFORMATION: Xaa = 1-Apc modified with acyl (Ac)
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with NH-hexyl
<220> FEATURE:
<221> NAME/KEY: MISC_FEATURE
<222> LOCATION: (10)..(10)
<223> OTHER INFORMATION: Xaa = alpha-aminoisobutyric acid (Aib)
<220> FEATURE:
<221> NAME/KEY: MOD_RES
<222> LOCATION: (28)..(28)
```

<223> OTHER INFORMATION: AMIDATION

<400> SEQUENCE: 20

Xaa Xaa Glu Phe Leu Ser Pro Glu His Xaa Arg Val Gln Gln Arg Lys
1               5                   10                  15

Glu Ser Lys Lys Pro Pro Ala Lys Leu Gln Pro Arg
            20                  25

<210> SEQ ID NO 21
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (28)..(28)
<223> OTHER INFORMATION: AMIDATION

<400> SEQUENCE: 21

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 22
<211> LENGTH: 18
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (18)..(18)
<223> OTHER INFORMATION: AMIDATION

<400> SEQUENCE: 22

Gly Ser Ser Phe Leu Ser Pro Glu His Gln Arg Val Gln Gln Arg Lys
1               5                   10                  15

Glu Ser

<210> SEQ ID NO 23
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with n-octanoyl

<400> SEQUENCE: 23

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 24
<211> LENGTH: 28
<212> TYPE: PRT
<213> ORGANISM: Artificial
<220> FEATURE:
<223> OTHER INFORMATION: Peptidyl analog of ghrelin
<220> FEATURE:
<221> NAME/KEY: MISC_FEATURE
<222> LOCATION: (2)..(2)
<223> OTHER INFORMATION: Xaa = alpha-aminoisobutyric acid (Aib)
<220> FEATURE:
<221> NAME/KEY: MOD_RES
<222> LOCATION: (3)..(3)
<223> OTHER INFORMATION: modified with n-octanoyl
<220> FEATURE:
<221> NAME/KEY: MOD_RES
<222> LOCATION: (28)..(28)
<223> OTHER INFORMATION: free acid OH group

<400> SEQUENCE: 24

Gly Xaa Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 25
<211> LENGTH: 27
<212> TYPE: DNA
<213> ORGANISM: Artificial sequence
<220> FEATURE:
<223> OTHER INFORMATION: primer

<400> SEQUENCE: 25
atgtggaacg cgacgcccag cgaagag                                      27

<210> SEQ ID NO 26
<211> LENGTH: 27
<212> TYPE: DNA
<213> ORGANISM: Artificial sequence
<220> FEATURE:
<223> OTHER INFORMATION: primer

<400> SEQUENCE: 26
tcatgtatta atactagatt ctgtcca                                      27

<210> SEQ ID NO 27
<211> LENGTH: 6
<212> TYPE: PRT
<213> ORGANISM: Artificial sequence
<220> FEATURE:
<223> OTHER INFORMATION: Growth hormone releasing peptide
<220> FEATURE:
<221> NAME/KEY: MISC_FEATURE
<222> LOCATION: (2)..(2)
<223> OTHER INFORMATION: Xaa = D-Trp
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (6)..(6)
<223> OTHER INFORMATION: AMIDATION

<400> SEQUENCE: 27

His Xaa Ala Trp Xaa Lys
1               5

ANALOGS OF GHRELIN SUBSTITUTED AT THE N-TERMINAL

This application is a United States national stage filing under 35 U.S.C. §371 of international (PCT) application no. PCT/US2007/020595, filed Sep. 24, 2007, and designating the U.S., which claims priority to U.S. provisional application No. 60/847,423, filed Sep. 27, 2006.

BACKGROUND OF THE INVENTION

1. Field of the Invention

This invention relates to peptidyl analogs of ghrelin and their therapeutic use thereof.

2. Description of the Prior Art

Ghrelin, a recently discovered orexigenic hormone, is produced as a preprohormone that is proteolytically processed to yield a peptide of the following sequence: H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$ (Kojima, M. et al., *Nature*, (1999), 402(6762):656-60; SEQ ID NO:1). Ghrelin is produced by epithelial cells lining the fundus of the stomach and functions to stimulate appetite; its levels increase prior to a meal and decrease thereafter.

The native structures of ghrelin from several mammalian and non-mammalian species are known (Kaiya, H. et al., *J. Biol. Chem.*, (2001), 276(44):40441-8; and International Patent Application PCT/JP00/04907 [WO 01/07475]). A core region present in ghrelin is responsible for activity observed at the GHS receptor which comprises the four N-terminal amino acids wherein the serine in the third position is normally modified with n-octanoic acid. In addition to acylation by n-octanoic acid, native ghrelin may also be acylated with n-decanoic acid (Kaiya, H. et al., *J. Biol. Chem.*, (2001), 276(44):40441-8).

Ghrelin levels in the plasma of obese individuals are lower than those in leaner individuals and levels of ghrelin increase during the time of the day from midnight to dawn in thinner individuals suggesting a flaw in the circulatory systems of obese individuals (Yildiz, B. O. et al., *Proc. Natl. Acad. Sci. USA*, (2004), 101(28):10434-9). It has been found that individuals suffering from the eating disorder anorexia nervosa and patients who have cancer-induced cachexia have higher plasma levels of ghrelin (Garcia, J. M. et al., *J. Clin. Endocrin. Metab.*, (2005), 90(5):2920-6).

In both animals and humans, ghrelin powerfully stimulates growth hormone (GH) secretion from the anterior pituitary gland, mainly at the hypothalamic level, through its interaction with the GH secretagogue (GHS) receptor (GHS-R) (Ukkola, O. et al., *Ann. Med.*, (2002), 34(2):102-8; and Kojima, M. et al., *Nature*, (1999), 402(6762):656-60). The GH-releasing activity of ghrelin is mediated by activation of GHS receptors at the pituitary and mainly at the hypothalamic level (Kojima, M. et al., *Nature*, (1999), 402(6762):656-60).

Prior to the discovery that ghrelin is a native ligand for the GHS receptor, it was known that the pulsatile release of GH from the pituitary somatotrops is regulated by two hypothalamic neuropeptides: GH-releasing hormone (GHRH) and somatostatin. GHRH stimulates the release of GH whereas somatostatin inhibits the secretion of GH (Frohman, L. A. et al., *Endocr. Rev.*, (1986), 7(3):223-53; and Strobl, J. S. et al., *Pharmacology Review* (1994) 46:1-34). Ghrelin likely enhances the activity of GHRH-secreting neurons while concomitantly acting as a functional somatostatin antagonist (Ghigo, E. et al., *Eur. J. Endocri.*, (1997), 136(5):445-60).

Release of GH from the pituitary somatotrops can also be controlled by GH-releasing peptides (GHRP). The hexapeptide His-D-Trp-Ala-Trp-D-Phe-Lys-amide (GHRP-6; SEQ ID NO:27) was found to release GH from the somatotrops in a dose-dependent manner in several species, including man (Bowers, C. Y. et al., *Endocrinology*, (1984), 114(5):1537-45). Subsequent chemical studies on GHRP-6 led to the identification of other potent, synthetic GH secretagogues such as GHRP-I, GHRP-2 and hexarelin (Cheng, K. et al., *Endocrinology*, (1989), 124(6):2791-8; Bowers, C. Y., *Novel GH-Releasing Peptides, Molecular and Clinical Advances in Pituitary Disorders*, Ed: Melmed, S., Endocrine Research and Education, Inc., Los Angeles, Calif., USA, (1993), 153-7; and Deghenghi, R. et al., *Life Sci.*, (1994), 54(18):1321-8). The structures of these three compounds are:

```
                                           (SEQ ID NO: 2)
GHRP-I    Ala-His-D-(2')-Nal-Ala-Trp-D-Phe-Lys-NH2;

(SEQ ID NO: 3)
GHRP-2    D-Ala-D-(2')-Nal-Ala-Trp-D-Nal-Lys-NH2;
and (SEQ ID NO: 4)
Hexarelin His-D-2-MeTrp-Ala-Trp-D-Phe-Lys-NH2.
```

A GHS can stimulate secretion of GH by a different mechanism than that of GHRH (Bowers, C. Y. et al., *Endocrinology*, (1984), 114(5):1537-45; Cheng, K. et al., *Endocrinology*, (1989), 124(6):2791-8; Bowers, C. Y., *Novel GH-Releasing Peptides, Molecular and Clinical Advances in Pituitary Disorders*, Ed: Melmed, S., Endocrine Research and Education, Inc., Los Angeles, Calif., USA, (1993), 153-7; and Deghenghi, R. et al., *Life Sci.*, (1994), 54(18):1321-8).

The low oral bioavailability (<1%) of a peptidyl GHS encouraged the search for non-peptide compounds mimicking the action of GHRP-6 in the pituitary. Several benzolactams and spiroindanes have been reported to stimulate GH release in various animal species, including humans (Smith, R. G. et al., *Science*, (1993), 260(5114):1640-3; Patchett, A. A. et al., *Proc. Natl. Acad. Sci. USA*, (1995), 92(15):7001-5; Chen, M.-H. et al., *Bioorg. Mod. Chem. Letts.*, (1996), 6(18):2163-8). A specific example of a small spiroindane is MK-0677 (Patchett, A. A. et al., *Proc. Natl. Acad. Sci. USA*, (1995), 92(15):7001-5):

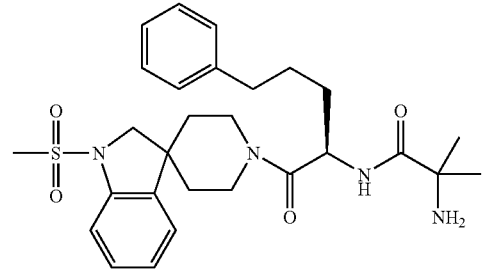

The actions of a GHS (both peptide and non-peptide) appear to be mediated by a specific GHS receptor (GHSR; Howard, A. D. et al., *Science*, (1996), 273(5277):974-7; and Pong, S. S. et al., *Mol. Endocri.*, (1996), 10(1):57-61). The GHS receptor is present in the pituitary and hypothalamus of various mammalian species (GHSR1a) and is distinct from the GH-releasing hormone receptor. The GHS receptor was also detected in the other areas of the central nervous system and in peripheral tissues, for instance, adrenal, thyroidal, cardiac, pulmonary, renal and muscular (Chen, M.-H. et al., *Bioorg. Med. Chem. Letts.*, (1996), 6(18):2163-9; Howard, A.

D. et al., *Science*, (1996), 273(5277):974-7; Pong, S. S. et al., *Mol. Endocri.*, (1996), 10(1):57-61; Guan, X.-M. et al., *Mol. Brain Res.*, (1997), 48(1):23-9; and McKee, K. K. et al., *Genomics*, (1997), 46(3):426-34). A truncated version of GHSR1a has been reported (Howard, A. D. et al., *Science*, (1996), 273(5277):974-7).

The GHS receptor is a G-protein coupled-receptor. The effects of GHS receptor activation include depolarization and inhibition of potassium channels, an increase in intercellular concentrations of inositol triphosphate (IP3) and a transient increase in the concentrations of intracellular calcium (Pong, S. S. et al., *Mol. Endocri.*, (1996), 10(1):57-61; Guan, X.-M. et al., *Mol. Brain Res.*, (1997), 48(1):23-9; and McKee, K. K. et al., *Genomics*, (1997), 46(3):426-34).

GHS molecules such as ghrelin and its analogs have a variety of different therapeutic (U.S. Pat. No. 6,566,337; Inui, A., FASEB J., (2004), 18(3):439-56; Muller, E. E. et al., *Neurobiol. Aging*, (2002), 23(5):907-19; Casanueva, F. F. et al., *Trends Endocrinol. Metab.*, (1999), 10(1):30-8; and Ankerson, M. et al., *Drug Discovery Today*, (1999), 4:497-506) and diagnostic uses. Compounds exhibiting agonist effects at the GHS receptor are indicated for improving a GH-deficient state (U.S. Pat. Nos. 6,861,409 and 6,967,237; and Casanueva, F. F. et al., *Trends Endocrinol. Metab*, (1999), 10(1):30-8), increasing muscle mass (U.S. Pat. Nos. 6,861,409 and 6,967,237) and/or physical strength (Ankerson, M. et al., *Drug Discovery Today*, (1999), 4:497-506), improving bone density (U.S. Pat. Nos. 6,861,409, 6,967,237 and 6,251,902; and Sibilia, V. et al., *Growth Horm. IGF Res.*, (1999), 9(4):219-27), treating osteoporosis (International Patent Application Nos. PCT/IB96/01353 [WO 97/24369] and PCT/IB98/00873 [WO 98/58947]; and Casanueva, F. F. et al., *Trends Endocrinol. Metab.*, (1999), 10(1):30-8), overcoming sexual dysfunction (U.S. Pat. No. 6,967,237; and Casanueva, F. F. et al., *Trends Endocrinol. Metab.*, (1999) 10(1):30-8), treating cardiovascular disease (International Patent Application Nos. PCT/IB96/01353 [WO 97/24369] and PCT/IB98/00873 [WO 98/58947]; U.S. Pat. No. 6,251,902; De Gennaro Colonna, V. et al., *Eur. J. Pharmacol.*, (1997), 334(2-3):201-7; and Casanueva, F. F. et al., *Trends Endocrinol. Metab.*, (1999), 10(1):30-8), relieving arthritis pain (Granado, M., *Am. J. Endo. Metab.*, (2005), 288:486-92), preventing or alleviating the onset of Alzheimer's disease (U.S. Pat. Nos. 6,686,359 and 6,566,337) and/or treating systemic lupus erythematosus or inflammatory bowel disease, e.g. Crohn's disease or ulcerative colitis (U.S. Patent Publication No. 2002/0013320).

Agonistic analogs of ghrelin can facilitate a gain in body weight (U.S. Pat. No. 6,967,237; Tschop, M. et al., *Nature*, (2000), 407(6806):908-13; and Tschop, M. et al., *Endocrinology*, (2002), 143(2):558-68) which in turn can be used to maintain a desired body weight (U.S. Pat. Nos. 6,861,409 and 6,967,237) and/or to recover physical function (U.S. Pat. Nos. 6,967,237 and 6,251,902; and International Patent Application No. PCT/IB96/01353 [WO 97/24369]).

Ghrelin also increases appetite (U.S. Pat. No. 6,967,237; and Okada, K. et al., *Endocrinology*, (1996), 137(11):5155-8). As such, ghrelin is often used to treat patients suffering from certain diseases or disorders or undertaking medicinal regimens which are traditionally accompanied with an undesirable weight loss such as: anorexia (U.S. Pat. No. 6,967, 237; and Tschop, M. et al., *Endocrinology*, (2002), 143(2):558-68), bulimia (U.S. Pat. No. 6,967,237), cachexia (U.S. Pat. Nos. 6,967,237 and 6,251,902), particularly cancer-induced cachexia (U.S. Pat. No. 6,967,237; International Patent Appln. No. PCT/DK2004/000529 [WO 05/014032]; and Tschop, M. et al., *Endocrinology*, (2002), 143:558-68), AIDS (U.S. Pat. Nos. 6,861,409 and 6,967,237; and Tschop, M. et al., *Endocrinology*, (2002), 143(2):558-68), wasting syndrome in the frail and/or elderly (U.S. Pat. Nos. 6,861,409 and 6,967,237; International Patent Application No. PCT/IB96/01353 [WO 97/24369]; and Ankerson, M. et al., *Drug Discovery Today*, (1999) 4:497-506) and chronic renal failure (Casanueva, F. F. et al., *Trends Endocri. Metab.*, (1999), 10(1):30-8). Medicinal treatments traditionally accompanied by a weight loss include chemotherapy, radiation therapy, temporary or permanent immobilization and/or dialysis (U.S. Pat. Nos. 6,967,237 and 6,251,902).

Obesity is a major risk factor for diabetes and a large fraction of non-insulin-dependent diabetes mellitus (otherwise referred to as "NIDDM") patients are obese. Both conditions are characterized by elevated circulating insulin levels and suppressed GH levels. GH treatment of GH-deficient adults (Jorgensen, J. O. et al., *Lancet*, (1989), 1(8649):1221-5), obese women (Richelsen, B. et al., *Am. J. Physiol.*, (1994), 266(2 Pt 1):E211-6) and elderly men (Rudman, D. et al., *Horm. Res.*, (1991), 36 (Suppl 1):73-81) has been shown to produce increases in lean body, hepatic and muscle mass while decreasing fat mass. Accordingly, administration of a ghrelin agonist is an attractive therapy for obesity except for the diabetogenic effects of GH (U.S. Pat. No. 6,251,902; Ankerson, M. et al., *Drug Discovery Today*, (1999) 4:497-506; and Casanueva, F. F. et al., *Trends Endocri. Metab.*, (1999), 10(1):30-8). Complications of diabetes such as retinopathy and/or for treating cardiovascular disorders (U.S. Pat. No. 6,967,237; and U.S. Patent Application Publication No. 2003/0211967) may be indirectly treated by ghrelin as well.

Peptides affecting the release of growth hormone (GH), such as GHRP-1, GHRP-2 and ghrelin, are also thought to exhibit gastrokinetic or "prokinetic" effects (U.S. Pat. No. 6,548,501; Peeters, T. L., *J. Physiol. Pharmacol.*, (2003), 54 (supp 4):95-103 and references therein; Trudel, L. et al, *J. Physiol. Gastrointest. Liver Physiol.*, (2002), 282:G948-52). As such, analogs of GH secretagogues have also been employed to promote gastrointestinal motility, particularly in patients suffering from decreased gastrointestinal motility resulting from post-operative ileus or from gastroparesis incidental to the onset of diabetes or a chronic diabetic state (U.S. Pat. No. 6,548,501).

Gastrointestinal (GI) motility is a coordinated neuromuscular process that transports nutrients through the digestive system (Scarpignato, C., *Dig. Dis.*, (1997), 15:112), the impairment of which may result in a variety of ailments including gastroesophageal reflux disease (GERD), gastroparesis (e.g., diabetic and post-surgical), irritable bowel syndrome (IBS), constipation (e.g. that associated with the hypomotility phase of IBS), emesis (e.g., that caused by cancer chemotherapy agents), ileus and colonic pseudo-obstruction (U.S. Pat. No. 6,548,501; U.S. Patent Application No. 20040266989). These various complications of interrupted GI motility contribute significantly to the health care burdens of industrialized nations (U.S. Pat. No. 6,548,501; Feighner, S. D. et al., *Science*, (1999), 284:2184-8).

"Ileus" refers to the obstruction of the bowel or gut, especially the colon (see, e.g., Dorland's Illustrated Medical Dictionary, p. 816, 27th ed. (W.B. Saunders Company, Philadelphia 1988)). Generally, any trauma to the bowel resulting in the release of inflammatory mediators leading to activation of inhibitory neural reflexes will result in the onset of ileus. Ileus may be diagnosed by the disruption of the normal coordinated movements of the gut, resulting in failure of the propulsion of intestinal contents (Resnick, J., *Am. J. of Gastroentero.*, (1997), 92:751; Resnick, J., *Am. J. of Gastroentero.*, (1997), 92:934). Ileus should be distinguished from constipation, which refers to infrequent or difficulty in evacuating the feces (see, e.g., *Dorland's Illustrated Medical Dictionary*, p. 375, 27th ed. (W.B. Saunders Company, Philadelphia 1988)).

Ileus may be brought about by a variety of causes such as parturition; intestinal ischaemia; retroperitoneal haematoma; intraabdominal sepsis; intraperitoneal inflammation, e.g., acute appendicitis, choecystitis, pancreatitis; fractures of the spine; ureteric colic; thoracic lesions; basal pneumonia; rib fractures; myocardial infarction; and metabolic disturbances. Post-partum ileus is a common problem for women in the period following childbirth and is thought to be caused by fluctuations in natural opioid levels as a result of birthing stress. Patients having undergone procedures such as major abdominal surgery including laparotomy for abdominal abscess or small intestinal transplantation (SITx), chest, pelvic or orthopedic surgery, often suffer from a period of transient impairment of bowel function called post-surgical or post-operative ileus (referred to hereinafter as POI).

POI commonly occurs for 24 to 72 hours following surgery. In some instances, the bowel dysfunction may become quite severe, lasting for more than a week and affecting more than one portion of the GI tract (Livingston, E. H. et al., *Digest. Dis. and Sci.*, (1990), 35:121). Gastrointestinal dysmotility associated with POI is generally most severe in the colon. POI is characterized by abdominal nausea, distension, vomiting, obstipation, inability to eat and cramps. POI not only delays the normal resumption of food intake after surgery and prolongs hospitalization, but also fosters postoperative complications, especially aspiration pneumonia.

The administration of opioid analgesics to a patient after surgery may often contribute to and/or exacerbate existing bowel dysfunction, thereby delaying recovery of normal bowel function. Since virtually all patients receive opioid analgesics, such as morphine or other narcotics for pain relief after surgery, particularly major surgery, current post-surgical pain treatment may actually slow recovery of normal bowel function, resulting in a delay in hospital discharge and increasing the cost of medical care.

Agents which act to affect gastrointestinal motility may also confer beneficial effects upon patients suffering from emesis. Emesis, or vomiting, is often preceded by retching and may be accompanied by dry heaves. Emesis may be caused by imbalances in the digestive tract, such as ileus, dyspepsia, or inflammation of the gastric wall, or by imbalances in the sensory system or brain, such as motion sickness, migraine or tumors. Emesis may be self-induced such as in anorexia or bulimia, and it may also occur in response to severe pain, emotional responses (e.g., to disagreeable sights or odors), or pregnancy. Emesis is a common complication following the administration of many medications, particularly anti-cancer treatments such as chemotherapy. Prolonged episodes or repetitive emesis may result in a variety of injuries to the organism, including dehydration and electrolyte imbalances (Quigley, E. M. et al., *Gastroentero.*, (2001), 120:263-86).

Agents which act to affect gastrointestinal motility may also confer beneficial effects upon patients suffering from gastroparesis. Gastroparesis, also called delayed gastric emptying, is a disorder in which the nerves to the stomach are damaged or stop working and the stomach takes too long to empty its contents. For example, following damage to the vagus nerve, the nerve which controls the movement of food through the digestive tract, the muscles of the stomach and intestines do not work normally and the movement of food is slowed or stopped. High blood glucose causes chemical changes in nerves and damages the blood vessels that carry oxygen and nutrients to the nerves. If blood glucose levels remain high over a long period of time, as is often the case in diabetes, the vagus nerve can be damaged; gastroparesis often occurs in people with type 1 diabetes or type 2 diabetes (Murray, C. D. et al., *Gut*, (2005), 54:1693-8).

The traditional therapies for impaired GI motility, such as that of ileus, gastroparesis and emesis, are considered ineffective. Current therapies for treating ileus include functional stimulation of the intestinal tract, stool softeners, laxatives such as Dulcolax®, lubricants, intravenous hydration, nasogastric suction, prokinetic agents, early enteral feeding, and nasogastric decompression. Nasogastric intubation to decompress the stomach has also traditionally been used to treat ileus.

Traditional pharmaceuticals used to treat impaired GI motility, such as that of ileus, include drugs that act to increase colonic motility, such as Leu13-motilin and prostaglandin F2 alpha, and prokinetic agents, such as Cisapride®. PROPULSID®, which contains Cisapride® monohydrate, is an oral gastrointestinal agent (U.S. Pat. No. 4,962,115) indicated for the symptomatic treatment of adult patients with nocturnal heartburn due to gastroesophageal reflux disease. Other prokinetic agents include, for example, metoclopramide, domperidone, ondansetron, tropisetron, mosapride and itopride. Other treatments include administering adenosine-antagonizing pyrazolopyridine compounds (U.S. Pat. No. 6,214,843); pituitary adenylate cyclase activating peptide (PACAP) receptor antagonist in combination with a vasoactive intestinal peptide (VIP) receptor antagonist (U.S. Pat. No. 6,911,430); fedotozine (U.S. Pat. No. 5,362,756); neuropeptides (U.S. Pat. No. 5,929,035); and proteinase-activated receptor-2 antagonists (U.S. Pat. No. 5,929,035). In extreme cases, ileus has been treated with surgical intervention to unblock the colon.

These therapeutic regimens, however, suffer from numerous problems. For instance, PROPULSID® was recently removed from the market due to its potential to induce cardiac arrhythmias (U.S. Pat. No. 6,548,501). Adolor Corporation is presently in phase III clinical trials for a therapy to treat postoperative ileus using Alvimopan (Entereg®). Adolor's therapy, however, utilizes opioid receptor antagonists which merely block the side effects of opiate analgesics, rather than actually relieving the ileus condition. The phase III trials demonstrate marginal efficacy and minimal applicability for the treatment of ileus, particularly postoperative ileus.

Furthermore, these prior art methods for treatment of impaired GI motility lack specificity for different types of impairments, e.g., postoperative ileus or post-partum ileus. Also, these prior art methods offer no means for the prevention of impaired GI motility, such as that of ileus, gastroparesis and emesis. If impaired GI motility, such as that of ileus, gastroparesis and emesis, could be prevented or more effectively treated, hospital stays, recovery times, and medical costs would be significantly decreased with the additional benefit of minimizing patient discomfort.

Drugs which selectively target gut motility to correct gastrointestinal dysfunction caused by postoperative ileus would be ideal candidates for preventing and/or treating post-surgical and post-partum ileus. Such drugs would also be excellent candidates for the treatment of gastroparesis and/or emesis, particularly emesis associated with chemotherapies or other drug induced gastrointestinal dysfunction. Of those, drugs that do not interfere with the effects of opioid analgesics would be of special benefit in that they may be administered simultaneously with drugs for pain management with limited side effects.

A number of recent studies have demonstrated the potential use of GHSs such as ghrelin, GHRP-6 and others to stimulate motor activity in the intestinal tract and to treat conditions such as ileus and emesis. For example, ghrelin and GHRP-6 have been shown to accelerate gastric emptying in rats and mice (Peeters, T. L., J. Physiol. Pharmacol., (2003), 54 (supp 4):95-103). In rats, ghrelin has been shown to reverse the delay of gastric emptying in a post-operative ileus model (Peeters, T. L., J. Physiol. Pharmacol., (2003), 54 (supp 4):95-103; Trudel, L. et al., J. Physiol. Gastrointest. Liver Physiol., (2002), 282(6):G948-52) and in laparectomized dogs, ghrelin was shown to improve POI in the treated animals (Trudel, L. et al, Peptides, (2003), 24:531-4). In septic mice, ghrelin and GHRP-6 accelerated gastric emptying although had little effect upon increasing transit in the small intestine (De Winter, B. Y. et al., Neurogastroenterol. Motil., (2004), 16:439-46).

In experiments designed to mimic hospitalization conditions for a human patient suffering from POI, laparectomized rats were exposed to opiates as well as ghrelin analog RC-1139 (Poitras, P. et al., Peptides, (2005), 26:1598-601). In an assay measuring gastric emptying, RC-1139 was shown to reverse POI in the control and laparectomized rats in the presence of morphine. It is thus believed that ghrelin exhibits gastrokinetic effects without interfering with opiate activity.

Ferrets exposed to the cytotoxic anti-cancer agent cisplatin exhibited significantly reduced occurrences of retching and vomiting following intracerebroventricular administration of ghrelin (Rudd, J. A. et al., Neurosci. Lett., (2006), 392:79-83) thus confirming the ability of ghrelin to reduce emesis in a manner consistent with its role in modulating gastro-intestinal functions. It is thought that ghrelin's role in modulating gastric motility is independent of the GH-secretory activation and may be mediated by the vagal-cholinergic muscarinic pathway (U.S. Patent Application No. 20060025566).

Ghrelin has also been shown to increase gastric emptying in patients with diabetic gastroparesis (Murray, C. D. et al., Gut, (2005), 54:1693-8).

It is interesting to note that in the studies referenced above, the ghrelin or ghrelin analog was administered using intraperitoneal (ip), intravenous (iv) or intracerebroventricular (icv) injection. Other disclosures (U.S. Pat. No. 6,548,501; U.S. Patent Application No. 20020042419; U.S. Patent Application No. 20050187237; U.S. Patent Application No. 20060025566) report on the oral administration of GHSs as a means to treat impaired gastrointestinal motility.

Very few compounds are known in the art to be useful for treating impaired GI motility and more compounds affecting gastrointestinal motility, e.g. stimulation of motility, would be highly desirable. Compounds affecting gastrointestinal kinetics are useful in the treatment of interruptions in normal GI functions such as ileus and emesis.

Paradoxically, ghrelin antagonists can also be used to achieve a beneficial effect in a patient (U.S. Patent Publication Nos. 2002/187938, 2003/0211967 and 2004/0157227; and U.S. Pat. No. 6,967,237). For example, compounds exhibiting antagonist effects at the GHS receptor to promote the suppression of GH secretion, e.g., antagonist analogs of ghrelin, are indicated to reverse excessive GH secretion (U.S. Patent Application Publication No. 2002/0187938), to facilitate weight loss in the non-obese (U.S. Pat. No. 6,967,237), to maintain an ideal weight and/or to decrease appetite (U.S. Pat. No. 6,967,237). Ghrelin antagonists can also be used to facilitate weight loss in an obese individual wherein said obesity is not due to the onset of NIDDM (U.S. Pat. No. 6,967,237; and U.S. Patent Application Publication No. 2003/0211967).

Excessive weight is a contributing factor to many diseases or conditions such as hypertension, dyslipidemia and cardiovascular disease (U.S. Patent Application Publication No. 2003/0211967; and U.S. Pat. No. 6,967,237) as well as gall stones, osteoarthritis (U.S. Pat. No. 6,967,237), certain cancers (U.S. Patent Application Publication Nos. 2003/0211967 and 2004/0157227; and U.S. Pat. No. 6,967,237) and Prader-Willi syndrome (U.S. Pat. No. 6,950,707; International Patent Application No. PCT/US2004/008385 [WO 04/084943]; Haqq, A. M. et al., J. Clin. Endocri. Metab., (2003), 88(1): 174-8; and Cummings, D. E. et al., Nat. Med., (2002), 8(7): 643-4). Ghrelin antagonists which facilitate weight loss would therefore reduce the likelihood of such diseases or conditions and/or comprise at least part of a treatment for such diseases or conditions. Antagonists of GHS molecules have also been disclosed to exhibit binding to tumorigenic tissue to result in a decrease in the number of tumorigenic cells in the target tissues, e.g. tumors in the lung, mammary glands, thyroid or pancreas (International Patent Application No. PCT/EP99/08662 [WO 00/29011]).

Native ghrelin, however, has a relatively short half-life limiting the available routes of administration and dose required to have an observable effect on feed intake and/or weight reduction. The apparent half-life of exogenous ghrelin in rats is reported to be 30 minutes (Tolle, V. et al., Endocrin., (2002), 143:1353-61) and in humans only 10 minutes (Nagaya, N. et al., Am. J. Physiol. Regul. Integr. Comp. Physiol., (2001), 280:R1483-R1487). Given the wide variety of beneficial effects that GHSs have to offer, there is a need in the art for effective, biologically-stable ghrelin analog molecules.

SUMMARY OF THE INVENTION

Ghrelin analogs described herein are active at the GHS receptor. The analogs can bind to the receptor and stimulate or inhibit GHS receptor activity. Ghrelin analogs have a variety of different uses including, but not limited to, being employed as a research tool or as a therapeutic agent.

It was discovered that ghrelin analogs substituted with synthetic amino acids isonipecotic acid (Inp) or

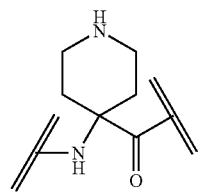

(1-Apc or 4-Apc) at the N-terminal exhibited better resistance to proteolysis compared to native ghrelin as well as increased activity at the GHS receptor.

The aspect of the present invention describes ghrelin analogs wherein the first amino acid listed in the definitions of $A^1$ to $A^{28}$ is the amino acid found at corresponding position in the sequence of native ghrelin, i.e. H-Gly-Ser-Ser-Phe-Leu-Ser-Pro-Glu-His-Gln-Arg-Val-Gln-Gln-Arg-Lys-Glu-Ser-Lys-Lys-Pro-Pro-Ala-Lys-Leu-Gln-Pro-Arg-NH$_2$ (SEQ ID NO:1), with the exception of the first amino acid in the sequence, i.e. the N-terminal residue, having the formula (I):

$$(R^2)-A^1-A^2-A^3-A^4-A^5-A^6-A^7-A^8-A^9-A^{10}-A^{11}-A^{12}-A^{13}-A^{14}-A^{15}-A^{16}-A^{17}-A^{18}-A^{19}-A^{20}-A^{21}-A^{22}-A^{23}-A^{24}-A^{25}-A^{26}-A^{27}-A^{28}-R^1 \qquad (I)$$

wherein:
$A^1$ is Inp, 1-Apc or 4-Apc;
$A^2$ is Ser, Abu, Acc, Act, Aib, Ala, Ava, Thr or Val;

$A^3$ is Ser, Asp(NH—$R^3$), Asp(O—$R^4$), Cys(S—$R^5$), Dab(S(O)$_2$—$R^6$), Dap(S(O)$_2$—$R^7$), Glu(NH—$R^8$), Glu(O—$R^9$), Ser(C(O)—$R^{10}$), Thr(C(O)—$R^{11}$) or HN—CH((CH$_2$)$_n$—N(R$^{12}$R$^{13}$))—C(O);

$A^4$ is Phe, Acc, Aic, Cha, 2-Fua, 1-Nal, 2-Nal, 2-Pal, 3-Pal, 4-Pal, hPhe, ($X^1,X^2,X^3,X^4,X^5$)Phe, Taz, 2-Thi, 3-Thi, Trp or Tyr;

$A^5$ is Leu, Abu, Acc, Aib, Ala, Cha, Ile, hLeu, Nle, Nva, Phe, Tle or Val;

$A^6$ is Ser, Abu, Acc, Act, Aib, Ala, Gly, Thr or Val;

$A^7$ is Pro, Dhp, Dmt, 3-Hyp, 4-Hyp, Inc, Ktp, Oic, Pip, Thz or Tic;

$A^8$ is Glu, Acc, Aib, Arg, Asn, Asp, Dab, Dap, Gln, Lys, Orn or HN—CH((CH$_2$)$_n$—N(R$^{12}$R$^{13}$))—C(O);

$A^9$ is His, Acc, Apc, Aib, 2-Fua, 2-Pal, 3-Pal, 4-Pal, ($X^1$,$X^2$,$X^3$,$X^4$,$X^5$-)Phe, Taz, 2-Thi or 3-Thi;

$A^{10}$ is Gln, Acc, Aib, Asn, Asp or Glu;

$A^{11}$ is Arg, Apc, hArg, Dab, Dap, Lys, Orn or HN—CH((CH$_2$)$_n$—N(R$^{12}$R$^{13}$))—C(O);

$A^{12}$ is Val, Abu, Acc, Aib, Ala, Cha, Gly, Ile, Leu, Nle, Nva or Tle;

$A^{13}$ is Gln, Acc, Aib, Asn, Asp or Glu;

$A^{14}$ is Gln, Acc, Aib, Asn, Asp or Glu;

$A^{15}$ is Arg, Acc, Aib, Apc, hArg, Dab, Dap, Lys or Orn;

$A^{16}$ is Lys, Acc, Aib, Apc, Arg, hArg, Dab, Dap, Orn or deleted;

$A^{17}$ is Glu, Arg, Asn, Asp, Dab, Dap, Gln, Lys, Orn, Asp(NH—$R^3$), Asp(O—$R^4$), Cys(S—$R^5$), Dab(S(O)$_2$—$R^6$), Dap(S(O)$_2$—$R^7$), Glu(NH—$R^8$), Glu(O—$R^9$), Ser(C(O)—$R^{10}$), Thr(C(O)—$R^{11}$), HN—CH((CH$_2$)$_n$—N(R$^{12}$R$^{13}$))—C(O) or deleted;

$A^{18}$ is Ser, Abu, Acc, Act, Aib, Ala, Thr, Val or deleted;

$A^{19}$ is Lys, Acc, Aib, Apc, Arg, hArg, Dab, Dap, Orn or deleted;

$A^{20}$ is Lys, Acc, Aib, Apc, Arg, hArg, Dab, Dap, Orn or deleted;

$A^{21}$ is Pro, Dhp, Dmt, 3-Hyp, 4-Hyp, Inc, Ktp, Oic, Pip, Thz, Tic or deleted;

$A^{22}$ is Pro, Dhp, Dmt, 3-Hyp, 4-Hyp, Inc, Ktp, Oic, Pip, Thz, Tic or deleted;

$A^{23}$ is Ala, Abu, Acc, Act, Aib, Apc, Gly, Nva, Val or deleted;

$A^{24}$ is Lys, Acc, Aib, Apc, Arg, hArg, Dab, Dap, Orn, HN—CH((CH$_2$)$_n$—N(R$^{12}$R$^{13}$))—C(O) or deleted;

$A^{25}$ is Leu, Abu, Acc, Aib, Ala, Cha, Ile, hLeu, Nle, Nva, Phe, Tle, Val or deleted;

$A^{26}$ is Gln, Aib, Asn, Asp, Glu or deleted;

$A^{27}$ is Pro, Dhp, Dmt, 3-Hyp, 4-Hyp, Inc, Ktp, Oic, Pip, Thz, Tic or deleted;

$A^{28}$ is Arg, Acc, Aib, Apc, hArg, Dab, Dap, Lys, Orn, HN—CH((CH$_2$)$_n$—N(R$^{12}$R$^{13}$))—C(O) or deleted;

$R^1$ is —OH, —NH$_2$, —(C$_1$-C$_{30}$)alkoxy or NH—$X^6$—CH$_2$-$Z^0$, wherein $X^6$ is a (C$_1$-C$_{12}$)alkyl or (C$_2$-C$_{12}$)alkenyl and $Z^0$ is —H, —OH, —CO$_2$H or —C(O)—NH$_2$;

$R^2$ is, H, (C$_1$-C$_{30}$)alkyl, (C$_1$-C$_{30}$)heteroalkyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_1$-C$_{30}$)acyl, substituted (C$_2$-C$_{30}$)alkenyl, substituted (C$_2$-C$_{30}$)alkynyl, substituted aryl(C$_1$-C$_{30}$)alkyl, substituted (C$_2$-C$_{30}$)alkynyl or substituted aryl(C$_1$-C$_{30}$)acyl;

each of $R^3$, $R^4$, $R^5$, $R^6$, $R^7$, $R^8$, $R^9$, $R^{10}$ and $R^{11}$ is, independently for each occurrence thereof, selected from the group consisting of (C$_1$-C$_{40}$)alkyl, (C$_2$-C$_{40}$)alkenyl, substituted (C$_1$-C$_{40}$) alkyl, substituted (C$_2$-C$_{40}$) alkenyl, alkylaryl, substituted alkylaryl, aryl and substituted aryl;

each of $R^{12}$ and $R^{13}$ is, independently for each occurrence thereof, selected from the group consisting of H, (C$_1$-C$_{40}$) alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroalkyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl(C$_1$-C$_{40}$)acyl, (C$_1$-C$_{40}$)alkylsulfonyl or —C(NH)—NH$_2$;

n is, independently for each occurrence thereof, 1, 2, 3, 4 or 5;

each of $X^1$, $X^2$, $X^3$, $X^4$, and $X^5$ is, independently for each occurrence thereof, selected from the group consisting of H, F, Cl, Br, I, (C$_{1-10}$)alkyl, substituted (C$_{1-10}$)alkyl, aryl, substituted aryl, OH, NH$_2$, NO$_2$ and CN;

provided that:

when $R^{12}$ is (C$_1$-C$_{40}$)acyl, aryl(C$_1$-C$_{40}$)acyl, substituted (C$_1$-C$_{40}$)acyl, substituted aryl(C$_1$-C$_{40}$)acyl, (C$_1$-C$_{40}$)alkylsulfonyl, or —C(NH)—NH$_2$, then $R^{13}$ is H or (C$_1$-C$_{40}$)alkyl, (C$_1$-C$_{40}$)heteroalkyl, (C$_2$-C$_{40}$)alkenyl, (C$_2$-C$_{40}$)alkynyl, aryl(C$_1$-C$_{40}$)alkyl, substituted (C$_1$-C$_{40}$)alkyl, substituted (C$_1$-C$_{40}$)heteroalkyl, substituted (C$_2$-C$_{40}$)alkenyl, substituted (C$_2$-C$_{40}$)alkynyl, or substituted aryl(C$_1$-C$_{40}$)alkyl;

or a pharmaceutically acceptable salt thereof.

A preferred group of compounds according to the above formula (I), termed Group 1 compounds, is where:

$A^2$ is Ser or Aib;
$A^3$ is Ser or Glu(NH—$R^8$);
$A^4$ is Phe;
$A^5$ is Leu;
$A^6$ is Ser;
$A^7$ is Pro;
$A^8$ is Glu or Aib;
$A^9$ is His;
$A^{10}$ is Gln or Aib;
$A^{11}$ is Arg;
$A^{12}$ is Val;
$A^{13}$ is Gln;
$A^{14}$ is Gln;
$A^{15}$ is Arg;
$A^{16}$ is Lys;
$A^{17}$ is Glu or Ser(C(O)—$R^{10}$);
$A^{18}$ is Ser;
$A^{19}$ is Lys;
$A^{20}$ is Lys;
$A^{21}$ is Pro;
$A^{22}$ is Pro;
$A^{23}$ is Ala;
$A^{24}$ is Lys;
$A^{25}$ is Leu;
$A^{26}$ is Gln;
$A^{27}$ is Pro; and
$A^{28}$ is Arg;

or a pharmaceutically acceptable salt thereof.

Another preferred group of compounds of the above formula, termed Group 2 compounds, is where:

$R^1$ is NH$_2$;
$R^2$ is H or acyl;
$R^8$ is hexyl; and
$R^{10}$ is octanyl;

or pharmaceutically acceptable salts thereof.

An even more preferred group of compounds of the immediate preceding group of compounds, identified to as Group 3 compounds, are compounds wherein:

$A^2$ is Aib;
$A^3$ is Glu(NH-hexyl);
$A^8$ is Aib;
$A^{10}$ is Aib; and
$A^{17}$ is Ser(n-octanoyl);

or a pharmaceutically acceptable salt thereof.

Another preferred group of compounds according to above-described formula (I), referred to throughout as Group 4 compounds, consists of compounds according to the formula:

(Inp¹)hGhrelin(1-28)-NH₂; (SEQ ID NO: 5)

(Inp¹, Aib²)hGhrelin(1-28)-NH₂; (SEQ ID NO: 6)

(Inp¹, Aib², Glu(NH-hexyl)3)hGhrelin(1-28)-NH₂; (SEQ ID NO: 7)

(Inp¹, Aib²,¹⁰)hGhrelin(1-28)-NH₂; (SEQ ID NO: 8)

(Inp¹, Aib²,⁸)hGhrelin(1-28)-NH₂; (SEQ ID NO: 9)

(Inp¹, Aib², Ser(n-octanoyl)¹⁷)hGhrelin(1-28)-NH₂; (SEQ ID NO: 10)

(Inp¹, Ser(n-octanoyl)¹⁷)hGhrelin(1-28)-NH₂; and (SEQ ID NO: 11)

(Inp¹, Aib²,⁸, Ser(n-octanoyl)¹⁷)hGhrelin(1-28)-NH₂; (SEQ ID NO: 12)

[Inp¹, Ser³]hGhrelin(1-28)-NH₂ (SEQ ID NO: 13)

[Inp¹, Aib², Ser³]hGhrelin(1-28)-NH₂ (SEQ ID NO: 14)

[Inp¹, Aib², Ser³, Ser(n-octanoyl)¹⁷]hGhrelin(1-28)-NH₂ (SEQ ID NO: 15)

[Inp¹, Aib²,¹⁰, Ser³]hGhrelin(1-28)-NH₂ (SEQ ID NO: 16)

or pharmaceutically acceptable salts thereof.

In one aspect, the preferred compound of the foregoing is (Inp¹)hGhrelin(1-28)-NH₂ (SEQ ID NO:5) or a pharmaceutically acceptable salt thereof. In another aspect, the preferred compound of the foregoing is (Inp¹, Aib², Ser(n-octanoyl)¹⁷) hGhrelin(1-28)-NH₂ (SEQ ID NO:10)) or a pharmaceutically acceptable salt thereof.

In one aspect, the present invention provides a pharmaceutical composition comprising an effective amount of a compound of the above formula, more preferably a compound according to one or more of Group 1, Group 2, Group 3 Group 4, (Inp¹)hGhrelin(1-28)-NH₂ (SEQ ID NO:5) and/or (Inp¹, Aib², Ser(n-octanoyl)¹⁷)hGhrelin(1-28)-NH₂ (SEQ ID NO:10), as defined hereinabove, or a pharmaceutically acceptable salt thereof and a pharmaceutically acceptable carrier or diluent.

Research tool applications generally involve the use of a ghrelin analog and the presence of a GHS receptor or fragment thereof. The GHS receptor can be present in different environments such as a mammalian subject, a whole cell or a membrane fragment. Examples of research tool applications include, but are not limited to, screening for compounds active at the GHS receptor, determining the presence of the GHS receptor in a sample or preparation and examining the role or effect of ghrelin.

Ghrelin analogs can be used to screen for both ghrelin agonists and ghrelin antagonists. Screening for ghrelin agonists can be performed, for example, by using a ghrelin analog in a competition experiment with test compounds. Screening for ghrelin antagonists can be performed, for example, by using a ghrelin analog to produce GHS receptor activity and then measuring the ability of a compound to alter GHS receptor activity.

Another aspect of the present invention features a method of screening for a compound able to bind to a GHS receptor. The method comprises the step of measuring the ability of a compound to affect binding of a ghrelin analog to the receptor, a fragment of the receptor comprising a ghrelin binding site, a polypeptide comprising the fragment or a derivative of the polypeptide. Compounds useful for screening include compounds of the above formula, more preferably compounds according to one or more of Group 1, Group 2, Group 3 Group 4, (Inp¹)hGhrelin(1-28)-NH₂ (SEQ ID NO:5) and/or (Inp¹, Aib², Ser(n-octanoyl)¹⁷)hGhrelin(1-28)-NH₂ (SEQ ID NO:10), as defined hereinabove, or a pharmaceutically acceptable salt thereof and a pharmaceutically acceptable carrier or diluent.

In another aspect, the invention provides a method of eliciting a response from a ghrelin receptor in a subject in need thereof which comprises administering to the subject a therapeutically effective amount of a ghrelin analog compound according to Group 1, Group 2, Group 3 Group 4, (Inp¹) hGhrelin(1-28)-NH₂ (SEQ ID NO:5) and/or (Inp¹, Aib², Ser (n-octanoyl)¹⁷)hGhrelin(1-28)-NH₂ (SEQ ID NO:10), as defined hereinabove, or pharmaceutically acceptable salts thereof, or a composition thereof as defined herein.

Another aspect of the present invention features a method for achieving a beneficial effect in a subject comprising administering to said subject an effective amount of one or more compounds according to the above formula, more preferably compounds according to one or more of Group 1, Group 2, Group 3 Group 4, (Inp¹)hGhrelin(1-28)-NH₂ (SEQ ID NO:5) and/or (Inp¹, Aib², Ser(n-octanoyl)¹⁷)hGhrelin(1-28)-NH₂ (SEQ ID NO:10), as defined hereinabove, or pharmaceutically acceptable salts thereof, or a composition thereof as defined herein, wherein said effective amount is effective for producing a beneficial effect in helping to treat (e.g., cure or reduce the severity) or to prevent (e.g., reduce the likelihood of onset or severity) a disease or disorder.

Ghrelin induces GH release from primary-culture pituitary cells in a dose-dependent manner without stimulating the release of the other pituitary hormones. Injected intravenously into anaesthetized rats, ghrelin stimulated the pulsatile release of GH (Kojima, M. et al., *Nature*, (1999), 402(6762): 656-60), thus another aspect of the present invention features a method for stimulating GH secretion in a subject in need thereof, comprising administering an effective amount of one or more of an agonist compound according to formula (I), more preferably an agonist compound according to one or more of Group 1, Group 2, Group 3 Group 4, (Inp¹)hGhrelin (1-28)-NH₂ (SEQ ID NO:5) and/or (Inp¹, Aib², Ser(n-octanoyl)¹⁷)hGhrelin(1-28)-NH₂ (SEQ ID NO:10), as defined hereinabove, or pharmaceutically acceptable salts thereof, or a composition thereof as defined herein, wherein said effective amount is at least an amount sufficient to produce a detectable increase in GH secretion and, preferably, is an amount sufficient to achieve a beneficial effect in a patient.

A preferred method of the immediately preceding method is wherein said stimulation of GH secretion is indicated for treating a GH deficient state, increasing muscle mass and/or bone density, overcoming sexual dysfunction, gaining body weight and/or maintaining an ideal body weight, maintaining and/or regaining physical functioning and/or increasing appetite.

A preferred method of the immediately preceding method is where said weight gain or maintenance thereof or appetite increase is indicated in a patient having a disease or disorder or under going a treatment accompanied by weight loss.

A preferred method of the immediately preceding method is where said disease accompanied by weight loss is associated with the cachexia which includes, but is not limited to, anorexia, bulimia, cancer, AIDS and chronic obstructive pulmonary disease (COPD). Another aspect of the immediately preceding method is wherein said weight loss is due to the onset of wasting syndrome, particularly in the frail or elderly. A further preferred method of the preceding method is to facilitate weight gain after an unexplained weight loss in an otherwise healthy elderly patient or to prevent, treat or alleviate the onset of Alzheimer's disease. In yet another preferred method of said immediately preceding method is where said treatments accompanied by weight loss include chemotherapy, radiation therapy, temporary immobilization, permanent immobilization and dialysis.

Another preferred method of the immediately preceding method is where said weight gain or maintenance thereof and/or appetite increase is indicated in an otherwise healthy patient not suffering from a particular disease or disorder or undergoing one of the aforementioned treatments.

In another aspect, the invention features a method of treating chronic obstructive pulmonary disease in a subject in need thereof comprising administering an effective amount of one or more of a compound according to formula (I), more preferably a compound according to one or more of Group 1, Group 2, Group 3 Group 4, (Inp$^1$)hGhrelin(1-28)-NH$_2$ (SEQ ID NO:5) and/or (Inp$^1$, Aib$^2$, Ser(n-octanoyl)$^{17}$)hGhrelin(1-28)-NH$_2$ (SEQ ID NO:10), as defined hereinabove, or pharmaceutically acceptable salts thereof, or a composition thereof as defined herein.

The present invention relates to a method of stimulating gastrointestinal motility in a patient (e.g., a mammal such as a human). The method includes the step of administering a therapeutically effective amount of one or more compounds, according to the above formula, more preferably compounds according to one or more of Group 1, Group 2, Group 3 Group 4, (Inp$^1$)hGhrelin(1-28)-NH$_2$ (SEQ ID NO:5) and/or (Inp$^1$, Aib$^2$, Ser(n-octanoyl)$^{17}$)hGhrelin(1-28)-NH$_2$ (SEQ ID NO:10), as defined hereinabove, or pharmaceutically acceptable salts thereof, or a composition thereof as defined herein, to said patient suffering from or at risk of gastrointestinal dysmotility.

In one aspect, the present invention provides a method of treating gastrointestinal dysmotility conditions by administering a therapeutically effective amount of a peptidyl analog of ghrelin or prodrug thereof suitable for attenuating such gastrointestinal conditions where the analog or prodrug comprises one or more compounds, according to the above formula, more preferably compounds according to one or more of Group 1, Group 2, Group 3 Group 4, (Inp$^1$)hGhrelin(1-28)-NH$_2$ (SEQ ID NO:5) and/or (Inp$^1$, Aib$^2$, Ser(n-octanoyl)$^{17}$)hGhrelin(1-28)-NH$_2$ (SEQ ID NO:10), as defined hereinabove, or pharmaceutically acceptable salts thereof, or a composition thereof as defined herein. The method of the invention is useful for promoting gastric and gastrointestinal motility in a patient (e.g., a mammal such as a human) and as such, is useful for treating conditions benefiting from improved gastric and gastrointestinal motility such as gastroesophageal reflux disease (GERD), irritable bowel syndrome (IBS), constipation, ileus, emesis, gastroparesis, colonic pseudo-obstruction, and the like.

In another aspect, the invention provides a method useful for promoting gastric and gastrointestinal motility in a patient (e.g., a mammal such as a human), by administering a therapeutically effective amount of one or more compounds, according to the above formula, more preferably compounds according to one or more of Group 1, Group 2, Group 3 Group 4, (Inp$^1$)hGhrelin(1-28)-NH$_2$ (SEQ ID NO:5) and/or (Inp$^1$, Aib$^2$, Ser(n-octanoyl)$^{17}$)hGhrelin(1-28)-NH$_2$ (SEQ ID NO:10), as defined hereinabove, or pharmaceutically acceptable salts thereof, or a composition thereof as defined herein, wherein the gastric dysmotility or ileus is associated with the administration of a opiate, such as, but not limited to, morphine.

In another aspect, the invention provides a method of treating ileus, gastroparesis or emesis by administering a therapeutically effective amount of one or more compounds, according to the above formula, more preferably compounds according to one or more of Group 1, Group 2, Group 3 Group 4, (Inp$^1$)hGhrelin(1-28)-NH$_2$ (SEQ ID NO:5) and/or (Inp$^1$, Aib$^2$, Ser(n-octanoyl)$^{17}$)hGhrelin(1-28)-NH$_2$ (SEQ ID NO:10), as defined hereinabove, or pharmaceutically acceptable salts thereof, or a composition thereof as defined herein, suitable for attenuating ileus, emesis, or gastroparesis. In yet another aspect, the condition treated by the method of the invention is ileus, such as post-operative ileus and the operation may be a gastrointestinal surgery such as abdominal surgery. The post-operative ileus may occur in any portion of the intestinal tract, for example, the stomach, small intestine or large intestine. The post-operative ileus may be accompanied by the presence of morphine. In another aspect the ileus is caused by a factor other than gastrointestinal surgery and may occur in any portion of the intestinal tract, for example, the stomach, small intestine or large intestine. In yet another aspect of the invention, the condition treated by the method of the invention is emesis, such as emesis associated with or provoked by the administration of an anti-cancer chemotherapeutic agent, pregnancy, bulimia, or anorexia. In yet another aspect, the condition treated by the method of the invention is gastroparesis, such as diabetic gastroparesis. The diabetes may be Type I or Type II diabetes.

In another aspect, the invention provides a method of performing surgery on a patient which comprises administering to said patient a therapeutically effective amount of one or more compounds, according to the above formula, more preferably compounds according to one or more of Group 1, Group 2, Group 3 Group 4, (Inp$^1$)hGhrelin(1-28)-NH$_2$ (SEQ ID NO:5) and/or (Inp$^1$, Aib$^2$, Ser(n-octanoyl)$^{17}$)hGhrelin(1-28)-NH$_2$ (SEQ ID NO:10), as defined hereinabove, or pharmaceutically acceptable salts thereof, or a composition thereof as defined herein. In one embodiment of the immediately foregoing, the method to perform surgery comprises identifying a patient in need of said surgery In one embodiment of the method of performing surgery, the surgery may directly or indirectly manipulate the gastrointestinal tract. The type of surgeries which may benefit from the method of the invention include, but are not limited to, laparotomy, transplant surgery, surgery to the urogenital system, surgery to the lymphatic system, surgery to the respiratory system, and surgery to treat cancer of any organ or tissue within the abdomen. The compounds useful to practice the method of performing surgery according to one or more of Group 1, Group 2, Group 3 Group 4, (Inp$^1$)hGhrelin(1-28)-NH$_2$ (SEQ ID NO:5) and/or (Inp$^1$, Aib$^2$, Ser(n-octanoyl)$^{17}$)hGhrelin(1-28)-NH$_2$ (SEQ ID NO:10), as defined hereinabove, or pharmaceutically acceptable salts thereof, or a composition thereof as defined herein may be administered before, during or after surgery, or any combination thereof.

In another aspect, the invention provides a method of preventing post-operative ileus in a patient in need thereof which comprises administering to said patient, before, during or after surgery, or any combination thereof, a therapeutically effective amount of one or more compounds, according to the above formula, more preferably compounds according to one or more of Group 1, Group 2, Group 3 Group 4, (Inp¹)hGhrelin(1-28)-NH$_2$ (SEQ ID NO:5) and/or (Inp¹, Aib², Ser(n-octanoyl)¹⁷)hGhrelin(1-28)-NH$_2$ (SEQ ID NO:10), as defined hereinabove, or pharmaceutically acceptable salts thereof, or a composition thereof as defined herein.

In another aspect, the invention provides a method of preventing reflux disease, emesis, gastroparesis, irritable bowel syndrome, constipation, or colonic pseudo-obstruction in a patient in need there which comprises administering to said patient, a therapeutically effective amount of one or more compounds, according to the above formula, more preferably compounds according to one or more of Group 1, Group 2, Group 3 Group 4, (Inp¹)hGhrelin(1-28)-NH$_2$ (SEQ ID NO:5) and/or (Inp¹, Aib², Ser(n-octanoyl)¹⁷)hGhrelin(1-28)-NH$_2$ (SEQ ID NO:10), as defined hereinabove, or pharmaceutically acceptable salts thereof, or a composition thereof as defined herein. The emesis may be associated with anti-cancer chemotherapeutic agent treatment, pregnancy, bulimia, or anorexia. The gastroparesis may be associated with diabetes; the diabetes may be Type I or Type II diabetes.

A second most preferred group of compounds according to above-described formula (I), referred to throughout as Group 5 compounds, consists of compounds according to the formula:

(Inp¹, Aib²,¹⁰, Glu(NH-hexyl)³)hGhrelin(1-28)-NH$_2$; (SEQ ID NO: 17)

(1-Apc¹, Aib²,¹⁰, Glu(NH-hexyl)³)-hGhrelin(1-28)-NH$_2$; (SEQ ID NO: 18)

(Ac-Inp¹, Aib²,¹⁰, Glu(NH-hexyl)³)hGhrelin(1-28)-NH$_2$; (SEQ ID NO: 19)
and (Ac-1-Apc¹, Aib²,¹⁰, Glu(NH-hexyl)³)hGhrelin(1-28)-NH$_2$; (SEQ ID NO: 20)

or pharmaceutically acceptable salts thereof.

In one aspect, the preferred compound is Inp¹, Aib²,¹⁰, Glu(NH-hexyl)³)hGhrelin(1-28)-NH$_2$ (SEQ ID NO:17) or a pharmaceutically acceptable salt thereof. In another aspect, the preferred compound is (1-Apc¹, Aib²,¹⁰, Glu(NH-hexyl)³)-hGhrelin(1-28)-NH$_2$ (SEQ ID NO:18) or a pharmaceutically acceptable salt thereof. In another aspect, the preferred compound is (Ac-Inp¹, Aib²,¹⁰, Glu(NH-hexyl)³)hGhrelin(1-28)-NH$_2$ (SEQ ID NO:19) or a pharmaceutically acceptable salt thereof. In another aspect, the preferred compound is (Ac-1-Apc¹, Aib²,¹⁰, Glu(NH-hexyl)³)hGhrelin(1-28)-NH$_2$ (SEQ ID NO:20) or a pharmaceutically acceptable salt thereof.

In another aspect, the present invention provides a pharmaceutical composition comprising an effective amount of a compound of the above formula, more preferably a compound according to Group 5, as defined hereinabove, or a pharmaceutically acceptable salt thereof and a pharmaceutically acceptable carrier or diluent.

In one aspect, the invention provides a method of screening for a compound able to bind to a GHS receptor comprising measuring the ability of a compound to affect binding of a compound according to Group 5, as defined hereinabove, or pharmaceutically acceptable salts thereof, to the receptor, to a fragment of the receptor, to a polypeptide comprising the fragment of the receptor, or to a derivative of the polypeptide.

In another aspect, the invention provides a method of eliciting a response from a ghrelin receptor in a subject in need thereof which comprises administering to the subject a therapeutically effective amount of a ghrelin antagonist analog compound according to Group 5, as defined hereinabove, or pharmaceutically acceptable salts thereof, or a composition thereof as defined herein.

In another aspect, the invention provides a method for achieving a beneficial effect in a subject comprising administering to the subject an effective amount of a ghrelin analog compound according to Group 5, as defined hereinabove, or pharmaceutically acceptable salts thereof, or a composition thereof as defined herein, where the effective amount is effective for producing a beneficial effect in helping to cure or reduce the severity or reduce the likelihood of onset or severity a disease or disorder. In one aspect, the beneficial effect helps to cure or reduce the severity or reduce the likelihood of onset or severity a disease or disorder.

An overabundance of GH secretion has been clinically attributed to a number of diseases and or conditions. Another aspect of the present invention features a method for suppressing GH secretion in a subject in need thereof, comprising administering an effective amount of one or more compounds, according to Group 5, as defined hereinabove, or pharmaceutically acceptable salts thereof, or a composition thereof as defined herein, wherein said effective amount is at least an amount sufficient to produce a detectable decrease in GH secretion and, preferably, is an amount sufficient to achieve a beneficial effect in a patient.

Ghrelin antagonist compounds according to Group 5, as defined hereinabove, or pharmaceutically acceptable salts thereof, or a composition thereof as defined herein, can also be used to achieve a beneficial effect in a patient. A preferred method of the immediately preceding method is wherein said suppression of GH secretion is indicated to facilitate weight loss and/or a decrease in appetite, maintain an ideal body weight, reverse obesity, treat diabetes and its complications such as retinopathy, and/or improve cardiovascular disorders. Excessive weight is a contributing factor to different diseases including, but not limited to, hypertension, diabetes, dyslipidemia, cardiovascular disease, gall stone formation, osteoarthritis, Prader-Willi syndrome and/or certain forms of cancers. Loss of weight has been proven to reduce the likelihood of such diseases when part of the prescribed treatment for such diseases.

In another aspect, the invention provides a method for suppressing growth hormone secretion in a subject in need of such suppression, comprising the step of administering to a subject an effective amount of a ghrelin analog compound according to Group 5, as defined hereinabove, or pharmaceutically acceptable salts thereof, or a composition thereof as defined herein, where the effective amount is at least an amount sufficient to produce a detectable decrease in growth hormone secretion.

In one aspect of the immediately foregoing aspect, the suppression of growth hormone secretion is indicated for the treatment of a disease or condition characterized by excessive growth hormone secretion, for facilitation of loss of excessive body weight, for facilitation of appetite decrease, for facilitation of weight maintenance, for treating obesity, for treating diabetes, for treating complications of diabetes including retinopathy, or for treating cardiovascular disorders. In another aspect, the excessive weight is a contributing factor to a disease or condition including hypertension, diabetes, dyslipidemia, cardiovascular disease, gall stones, osteoarthritis and cancers. It is contemplated that the facilitation of loss of body weight reduces the likelihood of such diseases or conditions. In another aspect, the facilitation of loss of body weight comprises at least part of a treatment for such diseases or conditions. In another aspect, the excessive weight is due to Prader-Willi syndrome. In yet another aspect, obesity is treated.

The effective amount of one or more ghrelin analog compounds and compositions thereof according and suitable for use in practicing any aspect of the present invention may be administered to the subject in need thereof by any acceptable medical means, including but not limited to, intravenous, subcutaneous, or oral methods, or implantation of a sustained release formulation.

Other features and advantages of the present invention are apparent from the additional descriptions provided herein, including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

The present invention features ghrelin analogs which are resistant to proteolysis yet either promote, i.e., an agonist or suppress, i.e. an antagonist, ghrelin activity at the GHS receptor. As detailed above, the analogs of the instant invention are useful for the treatment of a wide variety of ailments in a subject.

A "subject", as used herein, refers to a mammalian or non-mammalian animal including, for example and without limitation, a human, a rat, a mouse or farm animal. Reference to a subject does not necessarily indicate the presence of a disease or disorder. The term "subject" includes, for example, a mammalian or non-mammalian animal being dosed with a ghrelin analog as part of an experiment, a mammalian or non-mammalian animal being treated to help alleviate a disease or disorder, and a mammalian or non-mammalian animal being treated prophylactically to retard or prevent the onset of a disease or disorder.

A "therapeutically acceptable amount" of a compound or composition of the invention, regardless of the formulation or route of administration, is that amount which elicits a desired biological response in a subject. The biological effect of the therapeutic amount may occur at and be measured at many levels in an organism. For example, the biological effect of the therapeutic amount may occur at and be measured at the cellular level by measuring the response at a receptor which binds ghrelin and/or a ghrelin analog, or the biological effect of the therapeutic amount may occur at and be measured at the system level, such as effecting an increase/decrease in the levels of circulating growth hormone. The biological effect of the therapeutic amount may occur at and be measured at the organism level, such as the alleviation of a symptom(s) or progression of a disease or condition in a subject. A therapeutically acceptable amount of a compound or composition of the invention, regardless of the formulation or route of administration, may result in one or more biological responses in a subject. In the event that the compound or composition of the invention is subject to testing in an in vitro system, a therapeutically acceptable amount of the compound or composition may be viewed as that amount which gives a measurable response in the in vitro system of choice.

The ghrelin agonists and antagonists described herein, such as those of Group 1, 2, 3, 4 and/or 5, are useful for increasing, decreasing and/or maintaining body weight in a subject in need there of. Body weight is often measured and used to determine a Body Mass Index ("BMI"). The BMI value for a subject is determined by calculating weight in kilograms divided by the square of height in meters. The BMI "normal" range, which is well known in the art, is 19-22. Individuals whose body-mass index falls below the "normal" range are more susceptible to disease and certain beneficial medical treatments such as chemotherapy, are less effective in individuals having a subnormal BMI.

As used herein, an obese subject or mammal is characterized as having a body weight approximately 20%, approximately 25%, approximately 30% or greater than the normal body weight for said subject. Normal body weight may be determined by a comparison of the weight of the subject at a prior point in time, such as when ghrelin levels were normal, or by a comparison of the ghrelin levels of the subject as compared to averages of other subjects of a similar age and/or condition.

As used herein, an overweight subject or mammal is characterized as having a body weight approximately 5% greater to approximately 20% greater than the normal body weight for said subject. Normal body weight may be determined by a comparison of the weight of the subject at a prior point in time, such as when ghrelin levels were normal, or by a comparison of the ghrelin levels of the subject as compared to averages of other subjects of a similar age and/or condition.

As used herein, a normal subject or mammal is characterized as having a body weight approximately 5% greater than to approximately 5% less than the normal body weight for said subject. Normal body weight may be determined by a comparison of the weight of the subject at a prior point in time, such as when ghrelin levels were normal, or by a comparison of the ghrelin levels of the subject as compared to averages of other subjects of a similar age and/or condition. A normal weight subject may have a BMI in the approximate range of 19-22.

As used herein, a lean subject or mammal is characterized as having a body weight approximately 5% to 30% or even 50% less than the normal body weight for said subject. Normal body weight may be determined by a comparison of the weight of the subject at a prior point in time, such as when ghrelin levels were normal, or by a comparison of the ghrelin levels of the subject as compared to averages of other subjects of a similar age and/or condition.

As used herein, the terms "treat", "treating" and "treatment" include palliative, curative and prophylactic treatment.

As used herein, "measurable" means the biologic effect is both reproducible and significantly different from the baseline variability of the assay.

"Proteolysis" as used herein, refers to the directed degradation, i.e. cleavage, of a peptide by the hydrolysis of a peptide bond by a proteolytic, cellular enzyme referred to as a protease.

Unless defined otherwise, all technical and scientific terms used herein have the same meaning as commonly understood by one of ordinary skill in the art to which this invention belongs. Also, all publications, patent applications, patents and other references mentioned herein are incorporated by reference.

Certain amino acids present in compounds of the invention can be and are represented herein as follows:

Nomenclature and Abbreviations

| Symbol | Meaning |
|---|---|
| Abu | α-aminobutyric acid |
| Acc | 1-amino-1-cyclo($C_3$-$C_9$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Act | denotes the structure |
| Aib | α-aminoisobutyric acid |
| Aic | 2-aminoindan-2-carboxylic acid |
| Ala or A | alanine |
| β-Ala | beta-alanine |
| Apc | denotes the structure: |
| Arg or R | arginine |
| hArg | homoarginine |
| Asn or N | asparagine |
| Asp or D | aspartic acid |
| Ava | 5-amino-n-valeric acid |
| Cha | β-cyclohexylalanine |
| Cys or C | cysteine |
| hCys | L-homocysteine |
| Dab | 2,4-diaminobutyric acid |
| Dap | 2,3-diaminopropionic acid |
| Dhp | 3,4-dehydroproline |
| Dmt | 5,5-dimethylthiazolidine-4-carboxylic acid |
| 2-Fua | β-(2-furyl)-alanine |
| Gln or Q | glutamine |
| Glu or E | glutamic acid |
| Gly or G | glycine |
| His or H | histidine |
| 3-Hyp | trans-3-hydroxy-L-proline, i.e., (2S,3S)-3-hydroxypyrrolidine-2-carboxylic acid |
| 4-Hyp | 4-hydroxyproline, i.e., (2S,4R)-4-hydroxypyrrolidine-2-carboxylic acid |
| Ile or I | isoleucine |
| Inc | indoline-2-carboxylic acid |
| Inp | isonipecotic acid |
| Ktp | 4-ketoproline |
| Leu or L | leucine |
| hLeu | homoleucine |
| Lys or K | lysine |
| Met or M | methionine |
| 1-Nal | β-(1-naphthyl)-L-alanine |
| 2-Nal | β-(2-naphthyl)-L-alanine |
| Nle | norleucine |
| Nva | norvaline |
| Oic | octahydroindole-2-carboxylic acid |
| Orn | ornithine |
| 2-Pal | β-(2-pyridinyl)alanine |
| 3-Pal | β-(3-pyridinyl)alanine |
| 4-Pal | β-(4-pyridinyl)alanine |
| Phe or F | phenylalanine |
| hPhe | homophenylalanine |
| Pip | pipecolic acid |
| Pro or P | proline |
| Ser or S | serine |

| Symbol | Meaning |
|---|---|
| Taz | β-(4-thiazolyl)alanine, i.e., 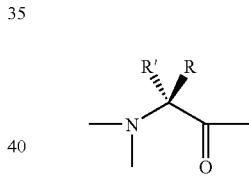 |
| 2-Thi | β-(2-thienyl)alanine |
| 3-Thi | β-(3-thienyl)alanine |
| Thp | 4-amino-4-carboxytetrahydropyran |
| Thr or T | threonine |
| Thz | thiazolidine-4-carboxylic acid |
| Tic | 1,2,3,4-tetrahydroisoquinoline-3-carboxylic acid |
| Tle | tert-leucine |
| Trp or W | tryptophan |
| Tyr or Y | tyrosine |
| Val or V | valine |

Where the amino acid has isomeric forms, it is the L form of the amino acid that is represented unless otherwise explicitly indicated.

The nomenclature used to define the peptides is that typically used in the art wherein the amino group at the N-terminus appears to the left and the carboxyl group at the C-terminus appears to the right, i.e., stand for the structure of —NH—CI(R')—CO—, wherein R and R' each is, independently, hydrogen or the side chain of an amino acid (e.g., R=$CH_3$ and R'=H for Ala), or R and R' may be joined to form a ring system. For the N-terminal amino acid, the abbreviation stands for the structure of:

or when the N-terminal amino acid is isonipecotic acid (Inp), the abbreviation stands for the structure of:

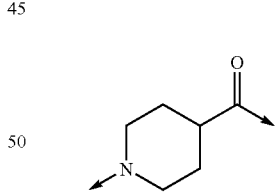

A peptide of this invention is also denoted herein by another format, e.g., (Aib$^2$)hGhrelin(1-28)-NH$_2$ (SEQ ID NO:21), with the substituted amino acid(s) from the natural sequence placed between the first set of parentheses (e.g., Aib$^2$ for Ser$^2$ in hGhrelin). The numbers between the second set of parentheses refer to the number of amino acids present in the peptide (e.g., hGhrelin(1-18) (SEQ ID NO:22) refers to amino acids 1 through 18 of the peptide sequence for human Ghrelin). The designation "NH$_2$" in e.g., (Aib$^2$)hGhrelin(1-28)-NH$_2$ (SEQ ID NO:21), indicates that the C-terminus of the peptide is amidated. (Aib$^2$)hGhrelin(1-28) (SEQ ID NO:23), or, alternatively, (Aib$^2$)hGhrelin(1-28)-OH (SEQ ID NO:24) indicates that the C-terminus is the free acid. A lower case letter is inserted before "Ghrelin" to indicate its source or origin, i.e. "h" indicates that the ghrelin is a homologue of the form of ghrelin found in homo sapiens.

Unless otherwise stated, those amino acids with a chiral center are provided in the L-enantiomer. Reference to "a derivative thereof" refers to a modified amino acid such as the corresponding D-amino acid, N-alkyl-amino acid, β-amino acid or labeled amino acid.

As used herein, Acc encompasses an amino acid selected from the group of 1-amino-1-cyclopropanecarboxylic acid (A3c); 1-amino-1-cyclobutanecarboxylic acid (A4c); 1-amino-1-cyclopentanecarboxylic acid (A5c); 1-amino-1-cyclohexanecarboxylic acid (A6c); 1-amino-1-cycloheptanecarboxylic acid (A7c); 1-amino-1-cyclooctanecarboxylic acid (A8c); and 1-amino-1-cyclononanecarboxylic acid (A9c).

"Acyl" refers to R"—C(O)—, where R" is H, alkyl, substituted alkyl, heteroalkyl, substituted heteroalkyl, alkenyl, substituted alkenyl, aryl, alkylaryl or substituted alkylaryl.

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Substituted alkyl" refers to an alkyl wherein one or more hydrogen atoms of the hydrocarbon group are replaced with one or more substituents selected from the group consisting of halogen (i.e., fluorine, chlorine, bromine and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present. The presence of —(CH$_2$)$_{0-20}$—COOH results in the production of an alkyl acid. Examples of alkyl acids containing, or consisting of —(CH$_2$)$_{0-20}$—COOH include, but are not limited to, 2-norbornane acetic acid, tert-butyric acid and 3-cyclopentyl propionic acid.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group is replaced with one or more substituents selected from the group consisting of halogen (i.e., fluorine, chlorine, bromine and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine and iodine), —OH, —CN, —SH, —NH$_2$, —NHCH$_3$, —NO$_2$, —C$_{1-20}$ alkyl substituted with 1 to 6 halogens, —CF$_3$, —OCH$_3$, —OCF$_3$ and —(CH$_2$)$_{0-20}$—COOH. In different embodiments 1, 2, 3 or 4 substituents are present.

"Aryl" refers to an optionally substituted aromatic group with at least one ring having a conjugated π-electron system, containing up to two conjugated or fused ring systems. Aryl includes, but is not limited to, carboxylic aryl, heterocyclic aryl and biaryl groups. Preferably, the aryl is a 5- or 6-membered ring. Preferred atoms for a heterocyclic aryl are one or more sulfur, oxygen and/or nitrogen. Examples of aryl include, but are not limited to, phenyl, 1-naphthyl, 2-naphthyl, indole, quinoline, 2-imidazole and 9-anthracene. Aryl substituents are selected from the group consisting of —C$_{1-20}$ alkyl, —C$_{1-20}$ alkoxy, halogen (i.e., fluorine, chlorine, bromine, and iodine), —OH, —CN, —SH, —NH$_2$, —NO$_2$, —C$_{1-20}$ alkyl substituted with 1 to 5 halogens, —CF$_3$, —OCF$_3$ and —(CH$_2$)$_{0-20}$—COOH. In different embodiments the aryl contains 0, 1, 2, 3 or 4 substituents.

The term "halo" encompasses fluoro, chloro, bromo and iodo.

The term "(C$_1$-C$_{12}$)hydrocarbon moiety" encompasses alkyl, alkenyl and alkynyl and in the case of alkenyl and alkynyl there are C$_2$-C$_{12}$.

"Alkylaryl" refers to an "alkyl" joined to an "aryl".

What is meant by Glu(NH-hexyl) is

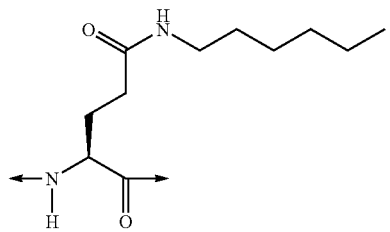

What is meant by Ser(n-octanoyl) or Ser(C(O)-heptyl) is

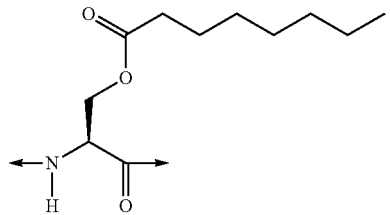

The N-terminal amino acids Inp and Apc have the structures of:

Inp:

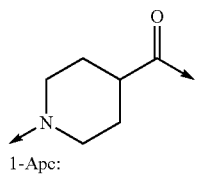

1-Apc:

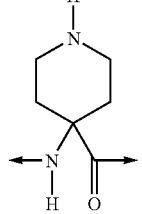

4-Apc:

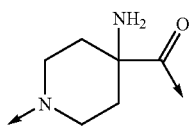

The present invention includes diastereomers as well as their racemic and resolved enantiomerically pure forms. Ghrelin analogs can contain D-amino acids, L-amino acids or any combination thereof. Preferably, amino acids present in a ghrelin analog are the L-enantiomers.

Preferred derivatives of analogs of the invention comprise D-amino acids, N-alkyl-amino acids, β-amino acids and/or one or more labeled amino acids (including a labeled version of a D-amino acid, N-alkyl-amino acids, or a β-amino acid). A labeled derivative indicates the alteration of an amino acid or amino acid derivative with a detectable label. Examples of detectable labels include luminescent, enzymatic and radioactive labels. Both the type of label and the position of the label can affect analog activity. Labels should be selected and positioned so as not to substantially alter the activity of the ghrelin analog at the GHS receptor. The effect of a particular label and position on ghrelin activity can be determined using assays measuring ghrelin activity and/or binding.

A protecting group covalently joined to the C-terminal carboxy group reduces the reactivity of the carboxy terminus under in vivo conditions. The carboxy terminus protecting group is preferably attached to the α-carbonyl group of the last amino acid. Preferred carboxy terminus protecting groups include amide, methylamide and ethylamide.
Certain other abbreviations used herein are defined as follows:
Nomenclature and Abbreviations

| Symbol | Meaning |
|---|---|
| Boc: | tert-butyloxycarbonyl |
| BSA: | bovine serum albumin |
| Bzl: | benzyl |
| DCM: | dichloromethane |
| DIC: | N,N-diisopropylcarbodiimide |
| DIEA: | diisopropylethyl amine |
| Dmab: | 4-{N-(1-(4,4-dimethyl-2,6-dioxocyclohexylidene)-3-methylbutyl)-amino} benzyl |
| DMAP: | 4-(dimethylamino)pyridine |
| DMF: | dimethylformamide |
| DNP: | 2,4-dinitrophenyl |
| EDTA | ethylenediaminetetracetic acid |
| Fmoc: | fluorenylmethyloxycarbonyl |
| HBTU: | 2-(1H-benzotriazole-1-yl)-1,1,3,3-tetramethyluronium hexafluorophosphate |
| cHex | cyclohexyl |
| HOAT: | O-(7-azabenzotriazol-1-yl)-1,1,3,3-tetramethyluronium hexafluorophosphate |
| HOBt: | 1-hydroxy-benzotriazole |
| HPLC: | high performance liquid chromatography |
| MBHA | 4-methylbenzhydrylamine |
| Mmt: | 4-methoxytrityl |
| NMP: | N-methylpyrrolidone |
| Pbf: | 2,2,4,6,7-pentamethyldihydrobenzofuran-5-sulfonyl |
| PhiPr | γ-2-phenylisopropyl ester |
| PyAOP: | 7-azabenzotriazol-1-yloxytris(pyrrolidino)phosphonium-hexafluorophosphate |
| tBu: | tert-butyl |
| TIS: | triisopropylsilane |
| TOS: | tosyl |
| trt | trityl |
| TFA: | trifluoro acetic acid |
| TFFH: | tetramethylfluoroforamidinium hexafluorophosphate |
| Z: | benzyloxycarbonyl |

Synthetic Methods

The compounds of the invention can be produced using the techniques disclosed in the examples herein as well as techniques that are well known in the art. For example, a polypeptide region of a ghrelin analog can be chemically or biochemically synthesized and modified. Examples of techniques for biochemical synthesis involving the introduction of a nucleic acid into a cell and expression of nucleic acids are provided in Ausubel, *Current Protocols in Molecular Biology*, John Wiley, 1987-1998 and Sambrook et al., in *Molecular Cloning, A Laboratory Manual,* 2nd Edition, Cold Spring Harbor Laboratory Press, 1989. Techniques for chemical synthesis of polypeptides are also well known in the art (Vincent in *Peptide and Protein Drug Delivery*, New York, N.Y., Dekker, 1990). For example, the peptides of this invention can be prepared by standard solid phase peptide synthesis (Stewart, J. M. et al., *Solid Phase Synthesis*, Pierce Chemical Co., 2d ed. 1984).

Substituent $R^2$ of the above generic formula may be attached to the free amine of the N-terminal amino acid by standard methods known in the art. For example, alkyl groups, e.g., $(C_1-C_{30})$alkyl, may be attached using reductive alkylation. Hydroxyalkyl groups, e.g., $(C_1-C_{30})$hydroxyalkyl, may also be attached using reductive alkylation wherein the free hydroxy group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for 1 hour. If the free acid contains a free hydroxy group, e.g., p-hydroxyphenylpropionic acid, then the coupling should be performed with an additional 3 molar equivalents of HOBT.

When $R^1$ is NH—$X^2$—$CH_2$—$CONH_2$, (i.e., $Z^0$=$CONH_2$), the synthesis of the peptide starts with Fmoc-HN—$X^2$—$CH_2$—COOH coupled to a Rink Amide-MBHA resin (Amide-4-methylbenzylhydryl amine obtained from Novabiochem®, San Diego, Calif.). If $R^1$ is NH—$X^2$—$CH_2$—COOH (i.e., $Z^0$-COOH) the synthesis of the peptide starts with Fmoc-HN—$X^2$—$CH_2$—COOH which is coupled to Wang resin.

In the synthesis of a ghrelin analogue of this invention containing A5c, A6c and/or Aib, the coupling time is two hours for these residues and the residue immediately following them.

Examples are provided below to further illustrate different features of the present invention. The examples also illustrate useful methodology for practicing the invention. These examples do not limit the claimed invention.

EXAMPLE 2

(Ac-1-Apc$^1$, Aib$^{2,10}$, Glu(NH-hexyl)$^3$)hGhrelin(1-28)-NH$_2$(SEQ ID NO:20)

Side chain protected Fmoc-(Aib$^{2,10}$,Glu$^3$) hGhrelin(2-28)-Rink amide-MBHA resin was synthesized on a 433A peptide synthesizer (obtained from Applied Biosystems®, Foster City, Calif., U.S.A.) using Fluorenylmethyloxycarbonyl (Fmoc) chemistry. A Rink Amide-4-methylbenzylhydrylamine (MBHA) resin (obtained from Novabiochem®, San Diego, Calif., U.S.A.) with substitution of 0.64 mmol/g was used. The Fmoc amino acids (obtained from AnaSpec®, San Jose, Calif., U.S.A.) used were Fmoc-Ala-OH, Fmoc-Arg (Pbf)-OH, Fmoc-Aib-OH, Fmoc-Gln(Trt)-OH, Fmoc-Glu (tBu)-OH, Fmoc-His(Trt)-OH, Fmoc-Leu-OH, Fmoc-Lys (Boc)-OH, Fmoc-Phe-OH, Fmoc-Pro-OH, Fmoc-Ser(tBu)-OH, and Fmoc-Val-OH. In addition, Fmoc-Glu(O-2-PhiPr)-OH (obtained from Novabiochem®, San Diego, Calif., U.S.A.) was used at $A^3$. The synthesis was carried out on a 0.1 mmol scale. The Fmoc groups were removed by treatment with 20% piperidine in N-methylpyrrolidone (NMP) for 30 minutes. In each coupling step, the Fmoc amino acid (3 eq, 0.3 mmol) was first pre-activated in a 2 mL solution of 0.45M 2-(1-H-benzotriazole-1-yl)-1,1,2,3-tetramethyluronium hexafluorophosphate/1-hydroxy-benzotriazole (HBTU/HOBT) in NMP. To the activated amino acid ester, 1 mL of diisopropylethylamine (DIEA) and 1 mL of NMP were added. The ABI 433A peptide synthesizer was programmed to perform the following:
(1) washing with NMP;
(2) removing Fmoc protecting group with 20% piperidine in NMP for 30 minutes;
(3) washing with NMP; and
(4) coupling with pre-activated Fmoc amino acid for one to three hours.

The resin was coupled successively according to the sequence of the title peptide. After the peptide chain was assembled, the resin was washed completely by using N,N-dimethylformamide (DMF) and dichloromethane (DCM).

At the end of the assembly of the peptide chain on the 433A, the peptide-resin was transferred to a reaction vessel on a shaker and the Fmoc was removed using 25% Pip/DMF for 30 min. The resin was washed with DMF. Fmoc-Apc-OH (0.4 mmole) was coupled using TFFH (tetramethylfluoroformamidinium hexafluorophosphate) (obtained from Perceptive Biosystems®, Warrington, U.K) (0.4 mmole), HOAt (0.4 mmol), DMAP (dimethylaminopyridine) (0.1 g) and DIEA (1.2 mmole) once for a four hour cycle and then again overnight.

The Fmoc group was removed as above and the peptide was capped using Ac2O (acetic anhydride) (5 mmole) and DIEA (5 mmole) in DMF for 30 minutes. The PhiPr groups were removed from $Glu^3$ using 2×3% TFA in DCM for a 10 minute cycle. The Boc that was partially removed from the side chain of Lys was replaced using Boc2O (0.8 mmole) and DIEA (0.8 mmole) in DCM overnight. The resin was then treated with PyAOP (7-azabenzotriazol-1-yloxytris (pyrrolidino) phosphonium-hexafluorophosphate) (obtained from Applied Biosystems®, Foster City, Calif., U.S.A.) (0.6 mmole), HOAt (0.6 mmole), DMAP (0.1 g) and DIEA (1.8 mmole) for a 10 minute cycle after which hexyl-$NH_2$, i.e., hexylamine (obtained from Sigma-Aldrich Chemicals®, St. Louis, Mo., U.S.A.) (2.0 mmole) was added and the resulting resin was continuously shaken overnight.

To cleave the title peptide, the resin was treated with a mixture of TFA, $H_2O$ and triisopropylsilane (TIS) (9.5 mL/0.85 mL/0.8 mL) for four hours. The resin was filtered off and the filtrate was poured into 200 mL of ether. The precipitate was collected by centrifugation. This crude product was dissolved in a mixture of acetonitrile and water and purified on a reverse-phase preparative HPLC system with a column (4×43 cm) of $C_{18}$ DYNAMAX-100 A° (obtained from Varian®, Walnut Creek, Calif., U.S.A.). The column was eluted over approximately 1 hour using a linear gradient of 92% A:8% B to 72% A:28% B, where A was 0.1% TFA in water and B was 0.1% TFA in acetonitrile. The fractions were checked by analytical HPLC and those containing pure product were pooled and lyophilized to dryness to give 1.5 mg (0.5%) yield of a white solid. Purity was assayed using HPLC and found to be approximately 97.5%. Electro-spray ionization mass spectrometry (ESI-MS) analysis gave the molecular weight at 3435.1 (in agreement with the calculated molecular weight of 3434.5).

EXAMPLE 4

$(1-Apc^1, Aib^{2,10}, Glu(NH-hexyl)^3)$-hGhrelin(1-28)-$NH_2$(SEQ ID NO:18)

Side chain protected Fmoc-($Aib^{2,10}$, $Glu^3$) hGhrelin(2-28)-Rink amide-MBHA resin was synthesized on a 433A peptide synthesizer (obtained from Applied Biosystems®, Foster City, Calif., U.S.A.) using Fluorenylmethyloxycarbonyl (Fmoc) chemistry. A Rink Amide-4-methylbenzylhydrylamine (MBHA) resin (obtained from Novabiochem®, San Diego, Calif., U.S.A.) with substitution of 0.64 mmol/g was used. The Fmoc amino acids (obtained from AnaSpec®, San Jose, Calif., U.S.A.) used were Fmoc-Ala-OH, Fmoc-Arg (Pbf)-OH, Fmoc-Aib-OH, Fmoc-Gln(Trt)-OH, Fmoc-Glu (tBu)-OH, Fmoc-His(Trt)-OH, Fmoc-Leu-OH, Fmoc-Lys (Boc)-OH, Fmoc-Phe-OH, Fmoc-Pro-OH, Fmoc-Ser(tBu)-OH, and Fmoc-Val-OH. In addition, Fmoc-Glu(O-2-PhiPr)-OH (obtained from Novabiochem®, San Diego, Calif.) was used at $A^3$. The synthesis was carried out on a 0.1 mmol scale. The Fmoc groups were removed by treatment with 20% piperidine in N-methylpyrrolidone (NMP) for a 30 minute cycle. In each coupling step, the Fmoc amino acid (3 eq, 0.3 mmol) was first pre-activated in 2 mL solution of 0.45M 2-(1-H-benzotriazole-1-yl)-1,1,2,3-tetramethyluronium hexafluorophosphate/1-hydroxy-benzotriazole (HBTU/HOBT) in NMP. To the activated amino acid ester, 1 mL of diisopropylethylamine (DIEA) and 1 mL of NMP were added to the resin. The ABI 433A peptide synthesizer was programmed to perform the following reaction:
(1) washing with NMP;
(2) removing Fmoc protecting group with 20% piperidine in NMP for 30 minutes;
(3) washing with NMP; and
(4) coupling with pre-activated Fmoc amino acid for one to four hours. The resin was coupled successively according to the sequence of the title peptide. After the peptide chain was assembled, the resin was washed completely by using N,N-dimethylformamide (DMF) and dichloromethane (DCM).

At the end of the assembly of the peptide chain on the 433A, the peptide-resin was transferred to a reaction vessel on a shaker and the Fmoc was removed by immersing in a solution of 25% Pip/DMF for approximately 30 minutes. The resin was thereafter washed with DMF. Fmoc-Apc-OH (0.4 mmole) was coupled using TFFH (tetramethylfluoroformamidinium hexafluorophosphate) (obtained from Perceptive Biosystems®, Warrington, U.K.) (0.4 mmole), HOAt (0.4 mmol), DMAP (dimethylaminopyridine) (0.1 g) and DIEA (1.2 mmole) for one four hour cycle and then again overnight.

The Fmoc group was removed as above. The PhiPr groups were removed from $Glu^3$ using two cycles of 3% TFA in DCM for a period of 10 minutes per cycle. The Boc that was partially removed from the side chain of Lys during the process was replaced using Boc2O (0.8 mmole) and DIEA (0.8 mmole) in DCM overnight. The resin was treated with PyAOP (7-Azabenzotriazol-1-yloxytris (pyrrolidino) phosphonium-hexafluorophosphate) (obtained from Applied Biosystems®, Foster City, Calif., U.S.A.) (0.6 mmole), HOAt (0.6 mmole), DMAP (0.1 g) and DIEA (1.8 mmole) for 10 minutes after which hexyl-$NH_2$, i.e., hexylamine, (obtained from Sigma-Aldrich Chemicals®, St. Louis, Mo., U.S.A.) (2.0 mmole) was added and the resin solution was shaken overnight.

The title peptide was cleaved from the resin by treating with a mixture of TFA, $H_2O$ and triisopropylsilane (TIS) (9.5 mL/0.85 mL/0.8 mL) for a period of approximately 4 hours. The resin was filtered off and the filtrate was poured into 200 mL of ether. The precipitate was collected by centrifugation. The crude product was dissolved in a mixture of acetonitrile and water and purified on a reverse-phase preparative HPLC system with a column (4×43 cm) of $C_{18}$ DYNAMAX-100 $A^0$ (obtained from Varian®, Walnut Creek, Calif., U.S.A.). The column was eluted over approximately one hour using a linear gradient of 92% A:8% B to 72% A:28% B, where A was 0.1% TFA in water and B was 0.1% TFA in acetonitrile. The fractions were checked by analytical HPLC and those containing pure product were pooled and lyophilized to dryness to give 4.6 mg (1.4%) of a white solid. Purity was assayed using HPLC and found to be approximately 99.8%. Electro-spray ionization mass spectrometry (ESI-MS) analysis gave the molecular weight at 3393.5 (in agreement with the calculated molecular weight of 3393.1).

EXAMPLE 11

($Inp^1$, Ser(n-octanoyl)$^{17}$)hGhrelin(1-28)-$NH_2$(SEQ ID NO:11)

Side chain protected Fmoc-($Ser^{17}$) hGhrelin(2-28)-Rink amide-MBHA resin was synthesized on a model 433A peptide synthesizer (obtained from Applied Biosystems®, Foster City, Calif., U.S.A.) using Fluorenylmethyloxycarbonyl (Fmoc) chemistry. A Rink Amide-4-methylbenzylhydrylamine (MBHA) resin (obtained from Novabiochem®, San Diego, Calif., U.S.A.) with substitution of 0.64 mmol/g was used. The Fmoc amino acids (obtained from AnaSpec®, San Jose, Calif., U.S.A.) used were Fmoc-Ala-OH, Fmoc-Arg (Pbf)-OH, Fmoc-Aib-OH, Fmoc-Gln(Trt)-OH, Fmoc-Glu (tBu)-OH, Fmoc-His(Trt)-OH, Fmoc-Leu-OH, Fmoc-Lys (Boc)-OH, Fmoc-Phe-OH, Fmoc-Pro-OH, Fmoc-Ser(tBu)-OH, and Fmoc-Val-OH. In addition, Fmoc-Ser(Trt)-OH (also obtained from AnaSpec®, San Jose, Calif., U.S.A.) was used at $A^3$ and $A^{17}$. The synthesis was carried out on a 0.2 mmol scale. The Fmoc groups were removed by treatment with 20% piperidine in N-methylpyrrolidone (NMP) for 30 minutes. In each coupling step, the Fmoc amino acid (3 eq, 0.3 mmol) was first pre-activated in 2 mL solution of 0.45M 2-(1-H-benzo-triazole-1-yl)-1,1,2,3-tetramethyluronium hexafluorophosphate/1-hydroxy-benzotriazole (HBTU/HOBT) in NMP. To the activated amino acid ester, 1 mL of diisopropylethylamine (DIEA) and 1 mL of NMP were added. The ABI 433A peptide synthesizer was programmed to perform the following:
(1) washing with NMP;
(2) removing Fmoc protecting group with 20% piperidine in NMP for 30 minutes;
(3) washing with NMP; and
(4) coupling with pre-activated Fmoc amino acid for 1 or 2 hours.
The resin was coupled successively according to the sequence of the title peptide. After the peptide chain was assembled, the resin was washed completely using N,N-dimethylformamide (DMF) and dichloromethane (DCM).

At the end of the assembly of the peptide chain on the 433A, the peptide-resin was transferred to a reaction vessel on a shaker and the Fmoc was removed using 25% Pip/DMF for a 30 minute cycle. The resin was washed with DMF. Fmoc-Inp-OH (1.0 mmole) was coupled using TFFH (tetramethylfluoroformamidinium hexafluorophosphate) (obtained from Perceptive Biosystems®, Warrington, U.K.) (1.0 mmole), HOAt ((1.0 mmol), DMAP (dimethylaminopyridine) (0.1 g) and DIEA (3.0 mmole) once overnight.

The Trt groups were removed from $Ser^3$ and $Ser^{17}$ using two cycles of 3% TFA in DCM each cycle lasting approximately 10 minutes. The Boc that was partially removed from the side chain of Lys as indicate above, was replaced using Boc2O (0.8 mmole) and DIEA (0.8 mmole) in DCM overnight. Octanoic acid (10 mmole) was coupled to the $Ser^3$ and $Ser^{17}$ side chains using DIC (5 mmole), DMAP (0.2 mg) and DIEA (5 mmole) in DCM overnight.

The terminal Fmoc was removed by immersion in 25% Pip/DMF for 30 minutes. The resin was then washed with DMF. The title peptide was cleaved from the resin using a mixture of TFA, $H_2O$ and triisopropylsilane (TIS) (9.5 mL/0.85 mL/0.8 mL) for approximately 4 hours. The resin was filtered off and the filtrate was poured into 200 mL of ether. The precipitate was collected by centrifugation. The crude product was dissolved in a mixture of acetonitrile and water and purified on a reverse-phase preparative HPLC system with a column (4×43 cm) of $C_{18}$ DYNAMAX-100 $A^0$ (obtained from Varian®, Walnut Creek, Calif., U.S.A.). The column was eluted over approximately 1 hour using a linear gradient of 85% A:15% B to 55% A:45% B, where A was 0.1% TFA in water and B was 0.1% TFA in acetonitrile. The fractions were checked by analytical HPLC and those containing pure product were pooled and lyophilized to dryness resulting in a 41.7 mg (5.9%) yield of a white solid. Purity was assayed using HPLC and found to be approximately 96.6%. Electro-spray ionization mass spectrometry (ESI-MS) analysis gave the molecular weight at 3507.4 (in agreement with the calculated molecular weight of 3508.16).

The following peptides of the invention can be prepared by a person of ordinary skill in the art using synthetic procedures analogous to those disclosed generally hereinabove:

```
Example 1:
                                        (SEQ ID NO: 19)
(Ac-Inp¹, Aib², ¹⁰, Glu(NH-hexyl)³)hGhrelin(1-28)-
NH₂;

Example 2:
                                        (SEQ ID NO: 20)
(Ac-1-Apc¹, Aib², ¹⁰, Glu(NH-hexyl)³)hGhrelin
(1-28)-NH₂;

Example 3:
                                        (SEQ ID NO: 17)
(Inp¹, Aib², ¹⁰, Glu(NH-hexyl)³)hGhrelin(1-28)-
NH₂;

Example 4:
                                        (SEQ ID NO: 18)
(1-Apc¹, Aib², ¹⁰, Glu(NH-hexyl)³)-hGhrelin(1-28)-
NH₂;

Example 5:
                                        (SEQ ID NO: 5)
(Inp¹)hGhrelin(1-28)-NH₂;

Example 6:
                                        (SEQ ID NO: 6)
(Inp¹, Aib²)hGhrelin(1-28)-NH₂;

Example 7:
                                        (SEQ ID NO: 7)
(Inp¹, Aib², Glu(NH-hexyl)³)hGhrelin(1-28)-NH₂;
```

-continued

Example 8:
(SEQ ID NO: 8)
(Inp$^1$, Aib$^{2, 10}$)hGhrelin(1-28)-NH$_2$;

Example 9:
(SEQ ID NO: 9)
(Inp$^1$, Aib$^{2, 8}$)hGhrelin(1-28)-NH$_2$;

Example 10:
(SEQ ID NO: 10)
(Inp$^1$, Aib$^2$, Ser(n-octanoyl)$^{17}$)hGhrelin(1-28)-NH$_2$;

Example 11:
(SEQ ID NO: 11)
(Inp$^1$, Ser(n-octanoyl)$^{17}$)hGhrelin(1-28)-NH$_2$;
and Example 12:
(SEQ ID NO: 12)
(Inp$^1$, Aib$^{2, 8}$, Ser(n-octanoyl)$^{17}$)hGhrelin(1-28)-NH$_2$.

Example 13:
(SEQ ID NO: 13)
[Inp$^1$, Ser$^3$]hGhrelin(1-28)-NH$_2$

Example 14:
(SEQ ID NO: 14)
[Inp$^1$, Aib$^2$, Ser$^3$]hGhrelin(1-28)-NH$_2$

Example 15:
(SEQ ID NO: 15)
[Inp$^1$, Aib$^2$, Ser$^3$, Ser(n-octanoyl)$^{17}$]hGhrelin(1-28)-NH$_2$ Example 16:
(SEQ ID NO: 16)
[Inp$^1$, Aib$^{2, 10}$, Ser$^3$]hGhrelin(1-28)-NH$_2$ A selection of the preferred embodiments listed above was analyzed by electro-spray ionization mass spectrometry (ESI-MS) to determine molecular weight. Table 1 presented below reports the data compiled during this testing. The purity of each of the selected compounds, assayed using HPLC, is also provided.

TABLE 1

Molecular Weight and Purity of Selected Compounds

| Example # | COMPOUND | Molecular Weight (Calculated) | Molecular Weight (MS-ES) | Purity (%) |
|---|---|---|---|---|
| #1 | (Ac-Inp$^1$, Aib$^{2, 10}$, Glu(NH-hexyl)3)hGhrelin(1-28)-NH$_2$ (SEQ ID NO: 19) | 3420.0 | 3419.5 | 97.0% |
| #2 | (Ac-1-Apc$^1$, Aib$^{2, 10}$, Glu(NH-hexyl)3)hGhrelin(1-28)-NH$_2$ (SEQ ID NO: 20) | 3435.5 | 3434.5 | 97.5% |
| #3 | (Inp$^1$, Aib$^{2, 10}$, Glu(NH-hexyl)3)hGhrelm(1-28)-NH$_2$ (SEQ ID NO: 17) | 3378.0 | 3377.6 | 97.8% |
| #4 | (1-Apc$^1$, Aib$^{2, 10}$, Glu(NH-hexyl)3)-hGhrelin(1-28)-NH$_2$ (SEQ ID NO: 18) | 3393.1 | 3393.5 | 99.8% |
| #5 | (Inp$^1$)hGhrelin(1-28)-NH$_2$ (SEQ ID NO: 5) | 3434.0 | 3423.8 | 96.2% |
| #6 | (Inp$^1$, Aib$^2$)hGhrelin(1-28)-NH$_2$ (SEQ ID NO: 6) | 3422.3 | 3422.1 | 99.0% |
| #7 | (Inp$^1$, Aib$^2$, Glu(NH-hexyl)3)hGhrelin(1-28)-NH$_2$ (SEQ ID NO: 7) | 3421.4 | 3421.3 | 99.0% |
| #8 | (Inp$^1$, Aib$^{2, 10}$)hGhrelin(1-28)-NH$_2$ (SEQ ID NO: 8) | 3379.0 | 3379.3 | 99.0% |
| #9 | (Inp$^1$, Aib$^{2, 8}$)hGhrelin(1-28)-NH$_2$ (SEQ ID NO: 9) | 3378.2 | 3377.4 | 98.0% |
| #10 | (Inp$^1$, Aib$^2$, Ser(n-octanoyl)$^{17}$)hGhrelin(1-28)-NH$_2$ (SEQ ID NO: 10) | 3506.2 | 3505.8 | 98.0% |
| #11 | (Inp$^1$, Ser(n-octanoyl)$^{17}$)hGhrelin(1-28)-NH$_2$ (SEQ ID NO: 11) | 3508.2 | 3507.4 | 96.6% |
| #12 | (Inp$^1$, Aib$^{2, 8}$, Ser(n-octanoyl)$^{17}$)hGhrelin(1-28)-NH$_2$ (SEQ ID NO: 12) | 3462.2 | 3462.3 | 99.0% |
| #13 | [Inp$^1$, Ser$^3$]hGhrelin(1-28)-NH$_2$ (SEQ ID NO: 13) | 3297.8 | 3298.2 | 99.5% |

TABLE 1-continued

Molecular Weight and Purity of Selected Compounds

| Example # | COMPOUND | Molecular Weight (Calculated) | Molecular Weight (MS-ES) | Purity (%) |
|---|---|---|---|---|
| #14 | [Inp$^1$, Aib$^2$, Ser$^3$]hGhrelin(1-28)-NH$_2$ (SEQ ID NO: 14) | 3295.8 | 3296.3 | 99.9% |
| #15 | [Inp$^1$, Aib$^2$, Ser$^3$, Ser(n-octanoyl)$^{17}$]hGhrelin(1-28)-NH$_2$ (SEQ ID NO: 15) | 3380.0 | 3380.9 | 99.0% |
| #16 | [Inp$^1$, Aib$^2$, 10, Ser$^3$]hGhrelin(1-28)-NH$_2$ (SEQ ID NO: 16) | 3252.8 | 3253.3 | 99.9 |

A selection of the preferred embodiments listed above was analyzed to determine stability, i.e. ½ life in plasma in a rat model using techniques known to those skilled in the art. Table 2 presented below reports the data compiled during such testing.

TABLE 2

Rat Plasma Life of Selected Compounds

| Example # | COMPOUND | Rat Plasma ½ life (in hours) |
|---|---|---|
| #1 | (Ac-Inp$^1$, Aib$^{2, 10}$, Glu(NH-hexyl)$^3$)hGhrelin(1-28)-NH$_2$ (SEQ ID NO: 19) | 9.4 |
| #3 | (Inp$^1$, Aib$^{2, 10}$, Glu(NH-hexyl)$^3$)hGhrelin(1-28)-NH$_2$ (SEQ ID NO: 17) | 10.6 |
| #4 | (1-Apc$^1$, Aib$^{2, 10}$, Glu(NH-hexyl)$^3$)-hGhrelin(1-28)-NH$_2$ (SEQ ID NO: 18) | 10.0 |
| #5 | (Inp$^1$)hGhrelin(1-28)-NH$_2$ (SEQ ID NO: 5) | 6.2 |
| #6 | (Inp$^1$, Aib$^2$)hGhrelin(1-28)-NH$_2$ (SEQ ID NO: 6) | 1.4 |
| #7 | (Inp$^1$, Aib$^2$, Glu(NH-hexyl)$^3$)hGhrelin(1-28)-NH$_2$ ((SEQ ID NO: 7) | 6.7 |
| #8 | (Inp$^1$, Aib$^{2, 10}$)hGhrelin(1-28)-NH$_2$ (SEQ ID NO: 8) | 1.2 |
| #9 | (Inp$^1$, Aib$^{2, 8}$)hGhrelin(1-28)-NH$_2$ (SEQ ID NO: 9) | 1.2 |
| #10 | (Inp$^1$, Aib$^2$, Ser(n-octanoyl)$^{17}$)hGhrelin(1-28)-NH$_2$ (SEQ ID NO: 10) | 0.6 |
| #11 | (Inp$^1$, Ser(n-octanoyl)$^{17}$)hGhrelin(1-28)-NH$_2$ (SEQ ID NO: 11) | 0.7 |
| #12 | (Inp$^1$, Aib$^{2, 8}$, Ser(n-octanoyl)$^{17}$)hGhrelin(1-28)-NH$_2$ (SEQ ID NO: 12) | 0.7 |

Determination of Biological Activity

Described herein are methods that can be and were used to characterize the compounds of the invention. The skilled artisan would know and appreciate the variations on these assays which would generate comparable results. The skilled artisan would also know and appreciate that other assays may be employed to generate the results and discern the characteristics described herein.

GHS Receptor Binding Determination Assay

The activity of the compounds of the invention at the GHS receptor can be and were determined using techniques such as those described in the examples provided below. With respect to IC$_{50}$, greater refers to potency and thus indicates a lesser amount is needed to achieve binding inhibition.

Binding assays can be performed using recombinantly produced GHS receptor polypeptides present in different environments. Such environments include, for example, cell extracts and purified cell extracts containing the GHS receptor polypeptide expressed from recombinant nucleic acid or naturally occurring nucleic acid; and also include, for example, the use of a purified GHS receptor polypeptide produced by recombinant means or from naturally occurring nucleic acid which is introduced into a different environment.

Screening for GHS Receptor Active Compounds

Screening for GHS receptor active compounds is facilitated using a recombinantly expressed receptor. A recombinantly expressed GHS receptor offers several advantages such as the ability to express the receptor in a defined cell system so that a response to a compound at the GHS receptor can more readily be differentiated from responses at other receptors. For example, the GHS receptor can be expressed in a cell line such as HEK 293, COS 7 and CHO not normally expressing the receptor by an expression vector wherein the same cell line without the expression vector can act as a control.

Screening for compounds reducing GHS receptor activity is facilitated using a ghrelin analog in the assay which provides for GHS receptor activity. The effect of test compounds on such activity can be measured to identify, for example, allosteric modulators and antagonists.

GHS receptor activity can be measured using different techniques such as detecting a change in the intracellular conformation of the GHS receptor, in the G-protein coupled activities and/or in the intracellular messengers. Preferably, GHS receptor activity is measured using techniques such as those measuring intracellular Ca$^{2+}$. Examples of techniques well known in the art that can be employed to measure Ca$^{2+}$ include the use of dyes such as Fura-2 and the use of Ca$^{2+}$- bioluminescent sensitive reporter proteins such as aequorin. An example of a cell line employing aequorin to measure G-protein activity is HEK293/aeq17 (Button, D. et al., *Cell Calcium*, (1993), 14(9):663-71; and Feighner, S. D. et al., *Science*, (1999), 284(5423):2184-8).

Chimeric receptors containing a ghrelin binding region functionally coupled to a different G-protein can also be used to measure GHS receptor activity. A chimeric GHS receptor contains an N-terminal extracellular domain, a transmembrane domain made up of transmembrane regions, extracellular loop regions and intracellular loop regions and an intracellular carboxy terminus. Techniques for producing chimeric receptors and measuring G-protein coupled responses are provided in, for example, International Patent Application No. PCT/US96/12336 [WO 97/05252] and U.S. Pat. No. 5,264,565 incorporated herein by reference.

Stimulation of GHS Receptor Activity

Ghrelin analogs can be used to stimulate GHS receptor activity which can be used, for example, to study the effects of GHS receptor modulation and/or GH secretion, to identify ghrelin antagonists and/or to benefit a subject suffering from a disease or condition such as a GH-deficient state, diminished muscle mass and/or bone density, sexual dysfunction, unhealthy body weight, loss of motor skills and/or physical functioning and/or a lack of normal appetite.

Increasing weight or appetite is crucial in maintaining an ideal, healthy body weight in an individual susceptible to weight loss, such as the sick or elderly. Loss of weight or appetite in an under weight subject can lead to serious health problems. In a patient suffering from a disease or undergoing a medical treatment which causes weight loss and/or a lack of normal appetite, the effectiveness of the treatment of said disease or condition is contingent upon the patient's ability to maintain a consistent weight.

Conversely, antagonists of ghrelin are useful in treatments to facilitate weight loss in those subjects for which weight loss is necessary.

Biological Assays

Examples

1. Receptor Binding Assay

1A. Preparation of CHO-K1 Cells Expressing the Human Recombinant GHS Receptor

The cDNA for human GH secretagogue receptor (hGHS-R or ghrelin receptor) was cloned using Polymerase Chain Reaction (PCR) techniques well known to those skilled in the art wherein human brain RNA was employed as a template (obtained from Clontech®, Palo Alto, Calif., U.S.A.), gene specific primers flanking the full-length coding sequence of hGHS-R(S: 5'-A T G T G G A A C G C G A C G C C C A G C G A A G A G-3' (SEQ ID NO:25) and AS:5'-T C A T G T A T T A A T A C T A G A T T C T G T C C A-3' (SEQ ID NO:26)) and Advantage 2 PCR Kit® (available from Clontech®, Palo Alto, Calif., U.S.A.). The PCR product was cloned into the pCR2.1 vector using Original TA Cloning Kit® (obtained from Invitrogen®, Carlsbad, Calif., U.S.A.). The full length human GHS-R was subcloned into the mammalian expression vector pcDNA 3.1 (available from Invitrogen®, Carlsbad, Calif., U.S.A.). The plasmid was transfected into the Chinese hamster ovary cell line, CHO-K1 (provided by American Type Culture Collection®, Rockville, Md., U.S.A.) using known calcium phosphate methods as described in Wigler, M. et al., *Cell*, (1977), 11(1):223-32. Single cell clones stably expressing the hGHS-R were obtained by selecting transfected cells grown in cloning rings in RPMI 1640 media supplemented with 10% fetal bovine serum and 1 mM sodium pyruvate containing 0.8 mg/ml G418 (purchased from Gibco®, Grand Island, N.Y., U.S.A.).

1B. GHS-R Binding Assay:

Membranes for radioligand binding studies can be and were prepared by homogenization of the foregoing CHO-K1 cells expressing the human recombinant GHS receptor in about 20 ml of ice-cold 50 mM Tris-HCl with a Brinkman Polytron® (Brinkman®, Westbury, N.Y., U.S.A.) at setting 6 for about 15 seconds. The homogenates were washed twice by centrifugation (39,000 g/10 minutes) and the final pellets were resuspended in about 50 mM Tris-HCl containing 2.5 mM $MgCl_2$ and 0.1% bovine serum albumin (BSA). For the selected assay, aliquots of approximately 0.4 ml were incubated with 0.05 nM ($^{125}$I)ghrelin (~2000 Ci/mmol; Perkin Elmer Life Sciences®, Boston, Mass., U.S.A.) with and without 0.05 ml of unlabeled competing test peptide. After approximately 60 minutes at 4° C., the bound ($^{125}$I)ghrelin was separated from the free ghrelin by rapid filtration through GF/C filters (available from Brandel®, Gaithersburg, Md., U.S.A.) which were pre-soaked in 0.5% polyethyleneimine/0.1% BSA. The filters were then washed 3 times with 5-ml aliquots of ice-cold 50 mM Tris-HCl and 0.1% BSA. The bound radioactivity trapped on the filters was counted by gamma spectrometry (using a spectrometer from Wallace LKB®, Gaithersburg, Md., U.S.A.). Specific binding was determined by subtracting ($^{125}$I)ghrelin bound in the presence of 1000 nM ghrelin (available from Bachem®, Torrence, Calif., U.S.A.) from the total ($^{125}$I)ghrelin bound.

A selection of the preferred embodiments was tested using the receptor binding assay discussed above and the results for those compounds are reported in Table 3 presented below.

TABLE 3

| Receptor Binding Ki Values for Selected Compounds | | | |
|---|---|---|---|
| Example # | COMPOUND | Ki (nM) | SEM |
| #1 | (Ac-Inp$^1$, Aib$^{2, 10}$, Glu(NH-hexyl)$^3$)hGhrelin(1-28)-NH$_2$ (SEQ ID NO: 19) | 370.00 | 18.18 |
| #2 | (Ac-1-Apc$^1$, Aib$^{2, 10}$, Glu(NH-hexyl)$^3$)hGhrelin(1-28)-NH$_2$ (SEQ ID NO: 20) | 39.99 | 10.92 |
| #3 | (Inp$^1$, Aib$^{2, 10}$, Glu(NH-hexyl)$^3$)hGhrelin(1-28)-NH$_2$ (SEQ ID NO: 17) | 0.10 | 0.04 |
| #4 | (1-Apc$^1$, Aib$^{2, 10}$, Glu(NH-hexyl)$^3$)-hGhrelin(1-28)-NH$_2$ (SEQ ID NO: 18) | 0.12 | 0.01 |
| #5 | (Inp$^1$)hGhrelin(1-28)-NH$_2$ (SEQ ID NO: 5) | 0.36 | 0.08 |
| #6 | (Inp$^1$, Aib$^2$)hGhrelin(1-28)-NH$_2$ (SEQ ID NO: 6) | 0.41 | 0.20 |
| #7 | (Inp$^1$, Aib$^2$, Glu(NH-hexyl)$^3$)hGhrelin(1-28)-NH$_2$ (SEQ ID NO: 7) | 0.33 | 0.04 |
| #8 | (Inp$^1$, Aib$^{2, 10}$)hGhrelin(1-28)-NH$_2$ (SEQ ID NO: 8) | 0.40 | 0.02 |

TABLE 3-continued

Receptor Binding Ki Values for Selected Compounds

| Example # | COMPOUND | Ki (nM) | SEM |
|---|---|---|---|
| #9 | (Inp$^1$, Aib$^{2,8}$)hGhrelin(1-28)-NH$_2$ (SEQ ID NO: 9) | 0.37 | 0.00 |
| #10 | (Inp$^1$, Aib2, Ser(n-octanoyl)$^{17}$)hGhrelin(1-28)-NH$_2$ (SEQ ID NO: 10) | 0.44 | 0.05 |
| #11 | (Inp$^1$, Ser(n-octanoyl)$^{17}$)hGhrelin(1-28)-NH$_2$ (SEQ ID NO: 11) | 0.49 | 0.02 |

2. GHS-R Functional Activity Assays

2A. In vitro GSH Receptor Mediated Intracellular iCa$^{2+}$ Mobilization

The foregoing CHO-K1 cells expressing the human GSH receptor were harvested by incubating in a 0.3% EDTA/phosphate buffered saline solution at 25° C.; the cells were then washed 2 times by centrifugation. The washed cells were resuspended in Hank's buffered saline solution (HBSS) for loading of the fluorescent Ca$^{2+}$ indicator Fura-2AM. Cell suspensions of approximately 10$^6$ cells/ml were incubated with 2 µM Fura-2AM for about 30 minutes at about 25° C. Unloaded Fura-2AM was removed by centrifugation twice in HBSS and the final suspensions were transferred to a spectrofluorometer (model Hitachi F-2000® Tokyo, Japan) equipped with a magnetic stirring mechanism and a temperature-regulated cuvette holder. After equilibration to 37° C., the ghrelin analogs were added for measurement of intracellular Ca$^{2+}$ mobilization. The excitation and emission wavelengths were 340 and 510 nm, respectively. An increase in the amount of Ca$^{2+}$ measured was indicative of agonist activity of a tested peptide while a decrease in the amount (or lack of) Ca$^{2+}$ measure was indicative of antagonist activity of a tested peptide.

Using this analysis method, compounds of Examples 1, 2, 3 and 4 were found to exhibit antagonistic activity at the ghrelin receptor.

2B. In Vivo GH Release/Suppression

As is well known in the art, compounds may be tested for their ability to stimulate or suppress release of GH in vivo (Deghenghi, R. et al., *Life Sciences*, (1994), 54(18):1321-8; and International Patent Application No. PCT/EP01/07929 [WO 02/08250]). In order to ascertain a compound's ability to stimulate GH release in vivo, a selected compound at a dosage of approximately 300 mg/kg is injected subcutaneously in 10-day old rats. The circulating GH is measured approximately 15 minutes after injection and compared to GH levels in rats injected with a solvent control.

Similarly, selected compounds may be tested for their ability to antagonize ghrelin-induced GH secretion in vivo. A 300 mg/kg dose of a compound of the instant application is injected subcutaneously in 10-day old rats along with ghrelin. The circulating GH is then measure approximately 15 minutes after injection and compared to GH levels in rats injected with ghrelin alone.

2C. Effect Upon Gastrointestinal Motility

Ghrelin has been shown to increase gastric motility and improve gastric emptying in subjects suffering from gastroparesis. Compounds of the invention can be tested to determine the effect of the compounds upon gastric emptying and intestinal transit using assays described below.

2C(i). In Vivo Study of Ghrelin on Intestinal Transit

The effect of native ghrelin and a peptidyl analog of ghrelin according to the instant inveiton on intestinal transit may be conducted. In such a study, groups of eight rats are fasted for approximately 24 hours with free access to water. Native ghrelin, a selected analog, or a control such as atropine is administered to anesthetized test subjects. Approximately five minutes after the initial administration of ghrelin, the selected analog or control, a 2 ml charcoal meal is administered to the test subjects by esophageal gavage. After approximately an additional 25 minutes, the test subjects are sacrificed by cervical rupture and the small intestines removed. The distance the charcoal traveled is measured from the pylorus.

2C(ii). In Vivo Study of Ghrelin on Gastric Emptying

Compounds of the invention can be tested to determine the effect of the compounds upon gastric emptying. In such a study, groups of eight male Sprague Dawley rats (weighing 200-250 gms) are fasted for approximately 24 hours with free access to water. Native ghrelin, a selected ghrelin analog and control compound such as metoclopramide are administered intravenously to anesthetized test subjects. Approximately five minutes after the initial administration of native ghrelin, the selected ghrelin analog or the control compound, a 1.5 ml meal marked with phenol red (0.5 mg/ml phenol red and 1.5% methyl cellulose in whole milk) is administered to each test subject by esophageal gavage. After approximately an additional 20 minutes, the test subjects are sacrificed by cervical rupture and the stomachs removed and individually pulverized. The residual phenol red in the stomach of the test subjects is extracted and measured spectrophometrically at a wavelength of 560 nm.

In other experiments, groups of eight male Sprague Dawley rats (weighing 200-250 gms) are fasted for approximately 24 hours with free access to water. The animals are injected subcutaneously with either vehicle or varying doses of native ghrelin or selected ghrelin analogs. After approximately 15 minutes, 1.5 ml of a phenol red marked nutrient meal (0.5 mg/ml phenol red & 1.5% methyl cellulose in whole milk) is administered orally to the rats. After an additional approximately 15 minutes, the subjects are sacrificed by cervical rupture and, after clamping the pylorus & cardia, the stomach removed. The residual phenol red in the stomach is extracted and measured by spectrophotometric methods at a wavelength of 560 nm.

2C(iii). Effect on POI in Rat

A 3 centimeter laparotomy is used to induce gastric ileus in male Sprague Dawley rats (weighing 200-250 gms) under isoflurane anesthesia. The abdominal muscles and skin are closed with suture and the animals are allowed to recover for approximately two hours and forty five minutes. At this time, vehicle or selected ghrelin analogs are administered subcutaneously to the laparectomized animals. Approximately 15 minutes after administration of the compounds or vehicle, a phenol red marked meal (see above) is introduced into the animals. After an additional approximately 15 minutes, the subjects are sacrificed by cervical rupture and gastric emptying is measured as described above.

2C(iv). Effect on POI in Rat in the Presence of Morphine

A 3 centimeter laparotomy is used to induce gastric ileus in male Sprague Dawley rats (weighing 200-250 gms) under isoflurane anesthesia. The abdominal muscles and skin are closed with suture and the animals are allowed to recover for approximately 2.5 hours at which time the laparecotomized animals receive a subcutaneous administration of 4 mg/kg morphine. Approximately 15 minutes after receiving the morphine, vehicle or selected ghrelin analogs are administered subcutaneously to the laparectomized animals. Approximately 15 minutes after administration of the compounds or vehicle, the phenol red marked meal (see above) is introduced into the animals. After an additional approximately 15 minutes, the subjects are sacrificed by cervical rupture and gastric emptying is measured as described above.

2C(v). Effect on Gastric Motility in Rat in the Presence of Morphine

Male Sprague Dawley rats (weighing 200-250 gms) receive a subcutaneous administration of 4 mg/kg morphine. Approximately 15 minutes after receiving the morphine, vehicle or selected ghrelin analogs are administered subcutaneously to the animals. Approximately 15 minutes after administration of the compounds or vehicle, a phenol red marked meal (see above) is introduced into the animals. After an additional approximately 15 minutes, the subjects are sacrificed by cervical rupture and gastric emptying was measured as described above.

2D. Effect Upon Weight

Ligands for melanocortin receptors of the present invention can be tested for an effect upon food intake and/or body weight according to the following procedures. One skilled in the art would know that procedures similar to those described herein may be used to assay the effect of the compounds of the invention upon food intake and/or body weight.

2D(i). Acute Feeding Experiments (Fasting)

Male Sprague Dawley rats (250 g) are housed in individual cages and maintained under 12:12 hour light:dark conditions. The rats are fasted for 18 hours prior to the start of the experiment with water available ad libitum. At time 0, the rats are injected subcutaneously (sc) with selected compounds at selected doses, for example, 500 or 100 nmole/kg, or with vehicle, and are provided with food. Individual food consumption is measured at about 1, 2, 3, 4, 5 and 6 hours after injection.

2D(ii). Acute Feeding Experiments (Non-fasting)

Male Sprague Dawley rats (250 g) are housed in individual cages and maintained under 12:12 hour light:dark conditions. Food and water is available ad libitum throughout the experiment. At time 0, the rats are injected sc with compound at doses of either 8 µmole/kg, or with vehicle. Individual food consumption is measured at about 0.5, 1, 1.5, 2, 3 and 4 hours after injection.

2D(iii) Chronic Feeding Experiments

Male Sprague Dawley rats (250 g) are housed in individual cages and maintained under 12:12 hour light:dark conditions with both food and water available ad libitum. The rats are injected 3×/day (0800, 1200, and 1600 h), sc, with compound at various doses or with vehicle for 7 days. Individual body weight and food consumption are measured daily.

Administration

Ghrelin analogs can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18$^{th}$ Edition, Ed. Gennaro, Mack Publishing, 1990, and *Modern Pharmaceutics 2nd Edition*, Eds. Banker and Rhodes, Marcel Dekker, Inc., 1990, both of which are hereby incorporated by reference.

Ghrelin analogs can be prepared as acidic or basic salts. Pharmaceutically acceptable salts (in the form of water- or oil-soluble or dispersible products) include conventional non-toxic salts or the quaternary ammonium salts formed from inorganic or organic acids or bases. Examples of such salts include, but are not limited to, acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine and salts with amino acids such as arginine and lysine.

Ghrelin analogs can be administered using different routes including oral and nasal ingestion or by transdermal and transmucosal injection. Active ingredients administered orally as a suspension can be prepared according to techniques well known in the art of pharmaceutical formulation and may contain microcrystalline cellulose for imparting bulk, alginic acid or sodium alginate as a suspending agent, methylcellulose as a viscosity enhancer and sweeteners/flavoring agents. As immediate release tablets, pharmaceutical formulations may contain microcrystalline cellulose, dicalcium phosphate, starch, magnesium stearate and lactose and/or other excipients, binders, extenders, disintegrants, diluents and lubricants.

Administered by nasal aerosol or inhalation formulations may be prepared, for example, as solutions in saline, employing benzyl alcohol or other suitable preservatives, absorption promoters to enhance bioavailability, employing fluorocarbons and/or employing other solubilizing or dispersing agents.

Ghrelin analogs may also be administered in intravenously (both bolus and infusion), intraperitoneally, subcutaneously, topically, with or without occlusion, or intramuscularly. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Ghrelin analogs can be provided in a kit. Such a kit typically contains an active compound in dosage forms for administration. A dosage form contains a sufficient amount of active compound such that a desirable effect can be obtained when administered to a subject during regular intervals, such as 1 to 6 times a day, during the course of 1 or more days. Preferably, a kit contains instructions indicating the use of the dosage form to achieve a desirable affect and the amount of dosage form to be taken over a specified time period.

The invention has been described in an illustrative manner, and it is to be understood that the terminology which has been used is intended to be in the nature of words of description rather than of limitation. Obviously, many modifications and variations of the present invention are possible in light of the above teachings. It is, therefore, to be understood that within the scope of the appended claims the invention may be practiced otherwise than as specifically described.

The patent and scientific literature referred to herein represents knowledge that is available to those with skill in the art. All patents, patent publications and other publications cited herein are hereby incorporated by reference in their entirety.

What is claimed is:

1. A ghrelin analog compound according to formula (I):

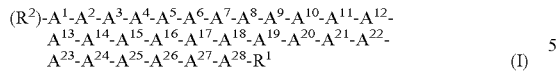
(I)

wherein:

$A^1$ is Inp, 1-Apc or 4-Apc;

$A^2$ is Ser, Abu, Acc, Act, Aib, Ala, Ava, Thr or Val;

$A^3$ is Ser, Asp(NH—$R^3$), Asp(O—$R^4$), Cys(S—$R^5$), Dab(S(O)$_2$—$R^6$), Dap(S(O)$_2$—$R^7$), Glu(NH—$R^8$), Glu(O—$R^9$), Ser(C(O)—$R^{10}$), Thr(C(O)—$R^{11}$) or HN—CH((CH$_2$)$_n$—N($R^{12}R^{13}$))—C(O);

$A^4$ is Phe, Acc, Aic, Cha, 2-Fua, 1-Nal, 2-Nal, 2-Pal, 3-Pal, 4-Pal, hPhe, ($X^1,X^2,X^3,X^4,X^5$)Phe, Taz, 2-Thi, 3-Thi, Trp or Tyr;

$A^5$ is Leu, Abu, Acc, Aib, Ala, Cha, Ile, hLeu, Nle, Nva, Phe, Tle or Val;

$A^6$ is Ser, Abu, Acc, Act, Aib, Ala, Gly, Thr or Val;

$A^7$ is Pro, Dhp, Dmt, 3-Hyp, 4-Hyp, Inc, Ktp, Oic, Pip, Thz or Tic;

$A^8$ is Glu, Acc, Aib, Arg, Asn, Asp, Dab, Dap, Gln, Lys, Orn or HN—CH((CH$_2$)$_n$—N($R^{12}R^{13}$))—C(O);

$A^9$ is His, Acc, Apc, Aib, 2-Fua, 2-Pal, 3-Pal, 4-Pal, ($X^1,X^2,X^3,X^4,X^5$-)Phe, Taz, 2-Thi or 3-Thi;

$A^{10}$ is Gln, Acc, Aib, Asn, Asp or Glu;

$A^{11}$ is Arg, Apc, hArg, Dab, Dap, Lys, Orn or HN—CH((CH$_2$)$_n$—N($R^{12}R^{13}$))—C(O);

$A^{12}$ is Val, Abu, Acc, Aib, Ala, Cha, Gly, Ile, Leu, Nle, Nva or Tle;

$A^{13}$ is Gln, Acc, Aib, Asn, Asp or Glu;

$A^{14}$ is Gln, Acc, Aib, Asn, Asp or Glu;

$A^{15}$ is Arg, Acc, Aib, Apc, hArg, Dab, Dap, Lys or Orn;

$A^{16}$ is Lys, Acc, Aib, Apc, Arg, hArg, Dab, Dap, Orn or deleted;

$A^{17}$ is Glu, Arg, Asn, Asp, Dab, Dap, Gln, Lys, Orn, Asp(NH—$R^3$), Asp(O—$R^4$), Cys(S—$R^5$), Dab(S(O)$_2$—$R^6$), Dap(S(O)$_2$—$R^7$), Glu(NH—$R^8$), Glu(O—$R^9$), Ser(C(O)—$R^{10}$), Thr(C(O)—$R^{11}$), HN—CH((CH$_2$)$_n$—N($R^{12}R^{13}$))—C(O) or deleted;

$A^{18}$ is Ser, Abu, Acc, Act, Aib, Ala, Thr, Val or deleted;

$A^{19}$ is Lys, Acc, Aib, Apc, Arg, hArg, Dab, Dap, Orn or deleted;

$A^{20}$ is Lys, Acc, Aib, Apc, Arg, hArg, Dab, Dap, Orn or deleted;

$A^{21}$ is Pro, Dhp, Dmt, 3-Hyp, 4-Hyp, Inc, Ktp, Oic, Pip, Thz, Tic or deleted;

$A^{22}$ is Pro, Dhp, Dmt, 3-Hyp, 4-Hyp, Inc, Ktp, Oic, Pip, Thz, Tic or deleted;

$A^{23}$ is Ala, Abu, Acc, Act, Aib, Apc, Gly, Nva, Val or deleted;

$A^{24}$ is Lys, Acc, Aib, Apc, Arg, hArg, Dab, Dap, Orn, HN—CH((CH$_2$)$_n$—N($R^{12}R^{13}$))—C(O) or deleted;

$A^{25}$ is Leu, Abu, Acc, Aib, Ala, Cha, Ile, hLeu, Nle, Nva, Phe, Tle, Val or deleted;

$A^{26}$ is Gln, Aib, Asn, Asp, Glu or deleted;

$A^{27}$ is Pro, Dhp, Dmt, 3-Hyp, 4-Hyp, Inc, Ktp, Oic, Pip, Thz, Tic or deleted;

$A^{28}$ is Arg, Acc, Aib, Apc, hArg, Dab, Dap, Lys, Orn, HN—CH((CH$_2$)$_n$—N($R^{12}R^{13}$))—C(O) or deleted;

$R^1$ is —OH, —NH$_2$, —(C$_1$-C$_{30}$)alkoxy or NH—$X^6$—CH$_2$—$Z^0$, wherein $X^6$ is a (C$_1$-C$_{12}$)alkyl or (C$_2$-C$_{12}$)alkenyl and $Z^0$ is —H, —OH, —CO$_2$H or —C(O)—NH$_2$;

$R^2$ is, H, (C$_1$-C$_{30}$)alkyl, (C$_1$-C$_{30}$)heteroallcyl, (C$_1$-C$_{30}$)acyl, (C$_2$-C$_{30}$)alkenyl, (C$_2$-C$_{30}$)alkynyl, aryl(C$_1$-C$_{30}$)alkyl, aryl(C$_1$-C$_{30}$)acyl, substituted (C$_1$-C$_{30}$)alkyl, substituted (C$_1$-C$_{30}$)heteroalkyl, substituted (C$_2$-C$_{30}$)acyl, substituted (C$_2$-C$_{30}$)alkenyl, substituted aryl(C$_1$-C$_{30}$)alkyl, substituted (C$_2$-C$_{30}$)alkynyl or substituted aryl(C$_1$-C$_{30}$)acyl;

each of $R^3, R^4, R^5, R^6, R^7, R^8, R^9, R^{10}$ and $R^{11}$ is, independently for each occurrence thereof, selected from the group consisting of (C$_1$-C$_{40}$)alkyl, (C$_2$-C$_{40}$)alkenyl, substituted (C$_1$-C$_{40}$) alkyl, substituted (C$_2$-C$_{40}$) alkenyl, alkylaryl, substituted alkylaryl, aryl and substituted aryl;

each of $R^{12}$ and $R^{13}$ is, independently for each occurrence thereof, selected from the group consisting of H, (C$_1$-C$_{40}$)alkyl, (C$_1$-C$_{40}$)heteroalkyl, (C$_1$-C$_{40}$)acyl, (C$_2$-C$_{40}$)alkenyl, (C$_2$-C$_{40}$)alkynyl, aryl(C$_1$-C$_{40}$)alkyl, aryl(C$_1$-C$_{40}$)acyl, substituted (C$_1$-C$_{40}$)alkyl, substituted (C$_1$-C$_{40}$)heteroallcyl, substituted (C$_1$-C$_{40}$)acyl, substituted (C$_2$-C$_{40}$)alkenyl, substituted (C$_2$-C$_{40}$)alkynyl, substituted aryl(C$_1$-C$_{40}$)alkyl, substituted aryl(C$_1$-C$_{40}$)acyl, (C$_1$-C$_{40}$)alkylsulfonyl or —C(NH)—NH$_2$;

n is, independently for each occurrence thereof, 1, 2, 3, 4 or 5;

each of $X^1, X^2, X^3, X^4$, and $X^5$ is, independently for each occurrence thereof, selected from the group consisting of H, F, Cl, Br, I, (C$_{1-10}$)alkyl, substituted (C$_{1-10}$)alkyl, aryl, substituted aryl, OH, NH$_2$, NO$_2$ and CN;

provided that:

when $R^{12}$ is (C$_1$-C$_{40}$)acyl, aryl(C$_1$-C$_{40}$)acyl, substituted (C$_1$-C$_{40}$)acyl, substituted aryl(C$_1$-C$_{40}$)acyl, (C$_1$-C$_{40}$)alkylsulfonyl, or —C(NH)—NH$^2$, then $R^{13}$ is H or (C$_1$-C$_{40}$)alkyl, (C$_1$-C$_{40}$)heteroalkyl, (C$_2$-C$_{40}$)alkenyl, (C$_2$-C$_{40}$)alkynyl, aryl(C$_1$-C$_{40}$)alkyl, substituted (C$_1$-C$_{40}$) alkyl, substituted (C$_1$-C$_{40}$)heteroalkyl, substituted (C$_2$-C$_{40}$)alkenyl, substituted (C$_2$-C$_{40}$)alkynyl, or substituted aryl(C$_1$-C$_{40}$)alkyl;

or a pharmaceutically acceptable salt thereof.

2. A compound according to claim 1, wherein:

$A^2$ is Ser or Aib;
$A^3$ is Ser or Glu(NH—$R^8$);
$A^4$ is Phe;
$A^5$ is Leu;
$A^6$ is Ser;
$A^7$ is Pro;
$A^8$ is Glu or Aib;
$A^9$ is His;
$A^{10}$ is Gln or Aib;
$A^{11}$ is Arg;
$A^{12}$ is Val;
$A^{13}$ is Gln;
$A^{14}$ is Gln;
$A^{15}$ is Arg;
$A^{16}$ is Lys;
$A^{17}$ is Glu or Ser(C(O)—$R^{10}$);
$A^{18}$ is Ser;
$A^{19}$ is Lys;
$A^{20}$ is Lys;
$A^{21}$ is Pro;
$A^{22}$ is Pro;
$A^{23}$ is Ala;
$A^{24}$ is Lys;
$A^{25}$ is Leu;
$A^{26}$ is Gln;
$A^{27}$ is Pro; and
$A^{28}$ is Arg;

or a pharmaceutically acceptable salt thereof.

3. A compound according to claim 2, wherein:

$R^1$ is NH$_2$;
$R^2$ is H or acyl;
$R^8$ is hexyl; and $R^{10}$ is octanyl;
or a pharmaceutically acceptable salt thereof.

4. A compound according to claim 3, wherein:
$A^2$ is Aib;
$A^3$ is Glu(NH-hexyl);
$A^8$ is Aib;
$A^{10}$ is Aib; and
$A^{17}$ is Ser(n-octanoyl);
or a pharmaceutically acceptable salt thereof.

5. A compound according to claim 4, wherein said compound is selected from the group consisting of:

```
                                                      (SEQ ID NO: 5)
(Inp¹)hGhrelin(1-28)-NH₂;

(SEQ ID NO: 6)
(Inp¹, Aib²)hGhrelin(1-28)-NH₂;

(SEQ ID NO: 7)
(Inp¹, Aib², Glu(NH-hexyl)³)hGhrelin(1-28)-NH₂;

(SEQ ID NO: 8)
(Inp¹, Aib², ¹⁰)hGhrelin(1-28)-NH₂;

(SEQ ID NO: 9)
(Inp¹, Aib², ⁸)hGhrelin(1-28)-NH₂;

(SEQ ID NO: 10)
(Inp¹, Aib², Ser(n-octanoyl)¹⁷)hGhrelin(1-28)-NH₂;

(SEQ ID NO: 11)
(Inp¹, Ser(n-octanoyl)¹⁷)hGhrelin(1-28)-NH₂;
and (SEQ ID NO: 12)
(Inp¹, Aib², ⁸, Ser(n-octanoyl)¹⁷)hGhrelin(1-28)-
NH₂;
``` or a pharmaceutically acceptable salt thereof.

6. A compound according to claim 1, wherein said compound is selected from the group consisting of:

```
                                                      (SEQ ID NO: 13)
[Inp¹, Ser³]hGhrelin(1-28)-NH₂;

(SEQ ID NO: 14)
[Inp¹, Aib², Ser³]hGhrelin(1-28)-NH₂;

(SEQ ID NO: 15)
[Inp¹, Aib², Ser³, Ser(n-octanoyl)¹⁷]hGhrelin
(1-28)-NH₂;
and (SEQ ID NO: 16)
[Inp¹, Aib², ¹⁰, Ser³]hGhrelin(1-28)-NH₂;
``` or a pharmaceutically acceptable salt thereof.

7. A pharmaceutical composition comprising an effective amount of a compound of according to claim 1, or a pharmaceutically acceptable salt thereof, and a pharmaceutically acceptable carrier or diluent.

8. A method for stimulating growth hormone secretion in a subject in need of such stimulation, comprising the step of administering to said subject a therapeutically effective amount of a ghrelin analog compound or pharmaceutically acceptable salt thereof according to claim 1 wherein said effective amount is at least an amount sufficient to produce a detectable increase in growth hormone secretion.

9. A method according to claim 8 wherein said stimulation of growth hormone secretion is indicated for treating a growth hormone deficient state, for increasing muscle mass, for increasing bone density, for treating sexual dysfunction in males or females, for facilitating a weight gain, for facilitating maintenance of weight, for facilitating maintenance of physical functioning, for facilitating recovery of physical function, or for facilitating appetite increase.

10. A method according to claim 9 wherein said facilitating weight gain, facilitating maintenance in weight, or facilitating appetite increase is indicated in a patient having a disease or disorder or undergoing a treatment accompanied by weight loss.

11. A method according to claim 10, wherein said weight loss is due to cachexia.

12. A method of treating chronic obstructive pulmonary disease in a subject in need thereof comprising administering to said subject a therapeutically effective amount of a ghrelin analog compound or pharmaceutically acceptable salt thereof according to claim 1.

13. A method of stimulating gastrointestinal motility in a subject in need thereof comprising administering to said subject a therapeutically effective amount of a ghrelin analog compound or pharmaceutically acceptable salt thereof according to claim 1.

14. A method according to claim 13, wherein said patient in need of gastrointestinal stimulation is suffering from gastroesophageal reflux disease, ileus, post-operative ileus, emesis, gastroparesis, inflammatory bowel syndrome (IBS), constipation, or colonic pseudo-obstruction.

15. A method according to claim 14, wherein said patient is suffering from ileus associated with the administration of an opiate.

16. A method according to claim 15, wherein said postoperative ileus follows abdominal surgery.

17. A method according to claim 16, wherein said ileus is of the stomach, small intestine, or large intestine.

18. A method according to claim 14, wherein said patient is suffering from emesis associated with treatment with an anti-cancer chemotherapeutic agent, pregnancy, bulimia, or anorexia.

19. A method according to claim 14, wherein said gastroparesis is associated with diabetes.

20. A method according to claim 13, wherein said therapeutically effective amount of said ghrelin analog compound or composition is administered intravenously, subcutaneously, orally, or by implantation of a sustained release formulation.

21. A method of treating post-operative ileus in a patient in need thereof, wherein said method comprises administering to said patient a therapeutically effective amount of a ghrelin analog compound or pharmaceutically acceptable salt thereof according to claim 1, before, during or after a surgery, or any combination thereof.

22. A method of treating gastroesophageal reflux disease, emesis, gastroparesis, irritable bowel syndrome (IBS), constipation, or colonic pseudo-obstruction in a patient in need thereof, wherein said method comprises administering to said patient a therapeutically effective amount of a ghrelin analog compound or pharmaceutically acceptable salt thereof according to claim 1.

23. A method of treating post-operative ileus, gastroesophageal reflux disease, emesis, gastroparesis, irritable bowel syndrome (IBS), constipation, or colonic pseudo-obstruction in a patient in need thereof by administering to said patient a therapeutically effective amount of a ghrelin analog compound or pharmaceutically acceptable salt thereof according to claim 1, wherein said administration is intravenous, subcutaneous, oral, or by implantation of a sustained release formulation.

24. A compound according to claim 1, wherein said compound is selected from the group consisting of:

(Ac-Inp$^1$, Aib$^{2, 10}$, Glu(NH-hexyl)$^3$)hGhrelin(1-28)-NH$_2$; (SEQ ID NO: 19)

(Ac-1-Apc$^1$, Aib$^{2, 10}$, Glu(NH-hexyl)$^3$)-hGhrelin(1-28)NH$_2$; (SEQ ID NO: 20)

(Inp$^1$, Aib$^{2, 10}$, Glu(NH-hexyl)$^3$)hGhrelin(1-28)-NH$_2$; and (SEQ ID NO: 17)

(1-Apc$^1$, Aib$^{2, 10}$, Glu(NH-hexyl)$^3$)-hGhrelin(1-28)NH$_2$; (SEQ ID NO: 18)

or a pharmaceutically acceptable salt thereof.

25. A pharmaceutical composition comprising an effective amount of a compound according to claim 24, or a pharmaceutically acceptable salt thereof, and a pharmaceutically acceptable carrier or diluent.

26. A method for suppressing growth hormone secretion in a subject in need of such suppression, comprising the step of administering to a subject an effective amount of a ghrelin analog compound according to claim 24, or a pharmaceutically acceptable salt thereof, wherein said effective amount is at least an amount sufficient to produce a detectable decrease in growth hormone secretion.

27. A method according to claim 26, wherein said suppression of growth hormone secretion is indicated for the treatment of a disease or condition characterized by excessive growth hormone secretion, for facilitation of loss of excessive body weight, for facilitation of appetite decrease, for facilitation of weight maintenance, for treating obesity, for treating diabetes, or for treating complications with diabetes including retinopathy.

* * * * *